United States Patent
Randle

(10) Patent No.: US 7,531,570 B2
(45) Date of Patent: May 12, 2009

(54) TREATMENT OF DISEASES USING ICE INHIBITORS

(75) Inventor: John C R Randle, Brookline, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 11/140,649

(22) Filed: May 27, 2005

(65) Prior Publication Data

US 2005/0267101 A1  Dec. 1, 2005

Related U.S. Application Data

(60) Provisional application No. 60/574,993, filed on May 27, 2004.

(51) Int. Cl.
  *A61K 31/40* (2006.01)
(52) U.S. Cl. .................................... 514/422
(58) Field of Classification Search ................ 514/422
  See application file for complete search history.

(56) References Cited

U.S. PATENT DOCUMENTS

| | | | |
|---|---|---|---|
| 4,465,679 A | 8/1984 | Huang et al. |
| 5,008,245 A | 4/1991 | Digenis et al. |
| 5,055,451 A | 10/1991 | Krantz et al. |
| 5,158,936 A | 10/1992 | Krantz et al. |
| 5,411,985 A | 5/1995 | Bills et al. |
| 5,416,013 A | 5/1995 | Black et al. |
| 5,430,128 A | 7/1995 | Chapman et al. |
| 5,434,248 A | * | 7/1995 | Chapman et al. ............ 530/330 |
| 5,462,939 A | 10/1995 | Dolle et al. |
| 5,463,124 A | 10/1995 | Jacobi et al. |
| 5,486,623 A | 1/1996 | Zimmerman et al. |
| 5,498,616 A | 3/1996 | Mallamo et al. |
| 5,498,695 A | 3/1996 | Daumy et al. |
| 5,519,113 A | 5/1996 | Jendralla et al. |
| 5,552,400 A | 9/1996 | Dolle et al. |
| 5,565,430 A | 10/1996 | Dolle et al. |
| 5,585,357 A | 12/1996 | Dolle et al. |
| 5,585,486 A | 12/1996 | Dolle et al. |
| 5,639,745 A | 6/1997 | Dolle et al. |
| 5,656,627 A | 8/1997 | Bemis et al. |
| 5,670,494 A | 9/1997 | Dolle et al. |
| 5,710,153 A | 1/1998 | Ohmoto et al. |
| 5,716,929 A | 2/1998 | Bemis et al. |
| 5,756,466 A | 5/1998 | Bemis et al. |
| 5,847,135 A | 12/1998 | Bemis et al. |
| 5,869,519 A | 2/1999 | Karanewsky et al. |
| 5,874,424 A | 2/1999 | Batchelor et al. |
| 5,877,197 A | 3/1999 | Karanewsky et al. |
| 5,973,111 A | 10/1999 | Bemis et al. |
| 6,008,217 A | 12/1999 | Batchelor et al. |
| 6,054,487 A | 4/2000 | Sekut et al. |
| 6,103,711 A | 8/2000 | Bemis et al. |
| 6,136,834 A | 10/2000 | Ohmoto et al. |
| 6,184,210 B1 | 2/2001 | Keana et al. |
| 6,184,244 B1 | 2/2001 | Karanewsky et al. |
| 6,187,771 B1 | 2/2001 | Karanewsky et al. |
| 6,197,750 B1 | 3/2001 | Karanewsky et al. |
| 6,204,261 B1 | 3/2001 | Batchelor et al. |
| 6,242,422 B1 | 6/2001 | Karanewsky et al. |
| 6,258,948 B1 | 7/2001 | Batchelor et al. |
| 6,376,484 B1 | 4/2002 | Ohmoto et al. |
| 6,420,522 B1 | 7/2002 | Bemis et al. |
| 6,531,474 B1 | 3/2003 | Wannamaker et al. |
| 6,632,942 B2 | 10/2003 | Robidoux |
| 6,632,962 B2 | 10/2003 | Golec et al. |
| 6,689,784 B2 | 2/2004 | Bebbington |
| 6,800,619 B2 | 10/2004 | Charrier et al. |
| 7,053,057 B2 | 5/2006 | Golec et al. |
| 7,074,782 B2 | 7/2006 | Bebbington |
| 7,205,327 B2 | 4/2007 | Kay et al. |
| 7,288,624 B2 | 10/2007 | Bemis et al. |
| 7,351,702 B2 | 4/2008 | Mortimore et al. |
| 7,358,273 B2 | 4/2008 | Wannamaker et al. |
| 7,417,029 B2 | 8/2008 | Wannamaker et al. |
| 2002/0045623 A1 | 4/2002 | Charrier et al. |
| 2002/0058630 A1 | 5/2002 | Charrier et al. |
| 2002/0169177 A1 | 11/2002 | Kay et al. |
| 2003/0092703 A1 | 5/2003 | Mortimore et al. |
| 2003/0096737 A1 | 5/2003 | Diu-Hercend et al. |
| 2005/0209162 A1 | 9/2005 | Roy et al. |
| 2005/0233974 A1 | 10/2005 | Randle et al. |

(Continued)

FOREIGN PATENT DOCUMENTS

EP  0 135 349  3/1985

(Continued)

OTHER PUBLICATIONS

McDermott et al., "The Autoinflammatory Syndromes", Current Opinion in Allergy and Clinical Immunology (2003).*

(Continued)

*Primary Examiner*—Kevin E Weddington
(74) *Attorney, Agent, or Firm*—Ropes & Gray LLP; James F. Haley, Jr.; Nina R. Horan

(57) ABSTRACT

This invention relates to methods and compositions for treating autoinflammatory diseases. The invention also assays for evaluating the ability of an ICE inhibitor to treat autoinflammatory diseases.

7 Claims, 5 Drawing Sheets

U.S. PATENT DOCUMENTS

| | | | |
|---|---|---|---|
| 2005/0233979 | A1 | 10/2005 | Charrier et al. |
| 2005/0272655 | A1* | 12/2005 | Mellis et al. ............... 514/12 |
| 2006/0128696 | A1 | 6/2006 | Vezzani et al. |
| 2007/0010457 | A1 | 1/2007 | Diu-Hercend et al. |
| 2008/0015172 | A1 | 1/2008 | Mortimore et al. |
| 2008/0039449 | A1 | 2/2008 | Batchelor et al. |
| 2008/0070953 | A1 | 3/2008 | Bemis et al. |

FOREIGN PATENT DOCUMENTS

| | | |
|---|---|---|
| EP | 0 410 411 | 1/1991 |
| EP | 0 417 721 | 3/1991 |
| EP | 0 525 420 | 2/1993 |
| EP | 0 528 487 | 2/1993 |
| EP | 0 529 713 | 3/1993 |
| EP | 0 533 226 | 3/1993 |
| EP | 0 547 699 | 6/1993 |
| EP | 0 618 223 | 10/1994 |
| EP | 0 623 592 | 11/1994 |
| EP | 0 644 197 | 3/1995 |
| EP | 0 644 198 | 3/1995 |
| EP | 0810221 | 12/1997 |
| WO | WO 91/015577 | 10/1991 |
| WO | WO 93/005071 | 3/1993 |
| WO | WO 93/009135 | 5/1993 |
| WO | WO 93/014777 | 8/1993 |
| WO | WO 93/016710 | 9/1993 |
| WO | WO 94/000154 | 1/1994 |
| WO | WO 94/003480 | 2/1994 |
| WO | WO 95/005192 | 2/1995 |
| WO | WO 95/026958 | 10/1995 |
| WO | WO 95/029672 | 11/1995 |
| WO | WO 95/031535 | 11/1995 |
| WO | WO 95/35308 | 12/1995 |
| WO | WO 95/035367 | 12/1995 |
| WO | WO 96/003982 | 2/1996 |
| WO | WO 96/025408 | 8/1996 |
| WO | WO 96/030395 | 10/1996 |
| WO | WO 96/033209 | 10/1996 |
| WO | WO 96/040647 | 12/1996 |
| WO | WO 97/007805 | 3/1997 |
| WO | WO 97/008174 | 3/1997 |
| WO | WO 97/22619 | 6/1997 |
| WO | WO 97/024339 | 7/1997 |
| WO | WO 98/001133 | 2/1998 |
| WO | WO 98/004539 | 3/1998 |
| WO | WO 98/010778 | 3/1998 |
| WO | WO 98/011109 | 3/1998 |
| WO | WO 98/011129 | 3/1998 |
| WO | WO 98/049189 | 11/1998 |
| WO | WO 99/47545 | 9/1999 |
| WO | WO 00/55114 | 9/2000 |
| WO | WO 00/55127 | 9/2000 |
| WO | WO 00/61542 | 10/2000 |
| WO | WO 01/05772 | 1/2001 |
| WO | WO 01/10383 | 2/2001 |
| WO | WO 01/16093 | 3/2001 |
| WO | WO 01/42216 | 6/2001 |
| WO | WO 01/72707 | 10/2001 |
| WO | WO 01/83458 | 11/2001 |
| WO | WO 01/90063 | 11/2001 |
| WO | WO 01/90070 | 11/2001 |
| WO | WO 01/94351 | 12/2001 |
| WO | WO 02/22611 | 3/2002 |
| WO | WO 02/094263 | 11/2002 |
| WO | WO 2005/047906 | 5/2005 |
| WO | WO 2005/085236 | 9/2005 |

OTHER PUBLICATIONS

NIH, Clinical Research Studies, Protocol No. 05-AR-0014 (2005).*

Grenier et al., "Functional screening of five PYPAF family members identifies PYPAF5 as a novel regulator of NF-κB and caspase-1," *FEBS Letters*, 530:73-78 (2002).

Hawkins et al., "Spectrum of clinical features in muckle-wells syndrome and response to Anakinra," *Arthritis and Rheumatism*, 50(2):607-612 (2004).

Hawkins et al., "Interleukin-1-receptor antagonist in the muckle-wells syndrome," *New England Journal of Medicine*, 348(25):2584 (2003).

M. Ator, "Peptide and Non-peptide inhibitors of interleukin-1Beta Converting Enzyme" Cambridge Healthtech Institute Inflammatory Cytokine Antagonists Targets, Strategies, and Indication, p. 1-15 (1994).

M.A. Ator and R. E. Dolle, "Interleukin-1β Converting Enzyme: Biology and the Chemistry of Inhibitors", Curr. Pharm. Design, 1, pp. 191-210 (1995).

K. Chapman, "Synthesis of a Potent, Reversible Inhibitor of Interleukin-1β Converting Enzyme", Bioorg. Med. Chem. Lett., 2, pp. 613-618 (1992).

R. Dolle et al., "Aspartyl α-((Diphenylphosphinyl)-oxy)methyl Ketones as Novel Inhibitors of Interleukin-1β Converting Enzyme. Utility of the Diphenylphosphinic Acid Leaving Group for the Inhibition of Cysteine Proteases", J. Med. Chem., 38, pp. 220-222 (1995).

R. Dolle et al., "Aspartyl α-((1-Phenyl-3-(trifluoromethyl)-pyrazol-5-yl)oxy)methyl Ketones as Interleukin-1β Converting Enzyme-Peptide Inhibitors. Significance of the P1 and P3 Amido Nitrogens for Enzyme-Peptide Inhibitor Binding", J. Med. Chem., 37, pp. 3863-3865 (1994).

R. Dolle et al., "P1 Aspartate-Based Peptide α-((2,6-Dichlorobenzoyl)oxy)methyl Ketones as Potent Time-Dependent Inhibitors of Interleukin-1β-Converting Enzyme", J. Med. Chem., 37, pp. 563-564 (1994).

P. Edwards et al., "Design, Synthesis, and Kinetic Evaluation of a Unique Class of Elastase Inhibitors, the Peptidyl α-Ketobenzoxazoles, and the X-ray Crystal Structure of the Covalent Complex between Porcine Pancreatic Elastase and Ac-Ala-Pro-Val-2-Benzoxazole", J. Am. Chem. Soc., 114, pp. 1854-1863 (1992).

P.R. Elford et al., "Reduction of Inflammation and Pyrexia in the Rat by Oral Administration of SDZ 224-015, an Inhibitor of the Interleukin-1β Converting Enzyme", Br. J. Pharmacology, 115, pp. 601-606 (1995).

T.P.D. Fan et al., "Stimulation of Angiogenesis by Substance P and Interleukin-1 in the Rat and Its Inhibition by NK1 or Interleukin-1 Receptor Antagonists", Br. J. Pharmacol., 110, 43-49 (1993).

I. Fauszt et al., "Inhibition of Interleukin-1beta Converting Enzyme by Peptide Derivatives," Proc. of the 13th Am. Peptide Symp., Jun. 20-25, 1993; Hodges, R.S. and Smith, J.A., Eds., Peptides, pp. 589-591 (1994).

D. Fletcher et al., "A Synthetic Inhibitor of Interleukin-1β Converting Enzyme Prevents Endotoxin-Induced Interleukin-1β Production In Vitro and In Vivo", J. Interfer. Cytokine Res., 15, pp. 243-248 (1995).

E. Frèrot et al., "PyBOP® and PyBroP: Two Reagents For the Difficult Coupling of the α, α-Dialkyl Amino Acid, Aib." Tetrahedron vol. 47, No. 2, pp. 259-270, (1991).

J. T. Gerig et al., "Attemped Synthesis of 2-Methylalanyl-L-prolyl-Ltryptophan An Unexpected Result." J. Org. Chem, vol. 41, No. 9, pp. 1653-1655, (1976).

T. Graybill et al., "The Preparation and Evaluation of Peptidic Aspartyl Hemiacetals as Reversible Inhibitors of ICE", Am. Chem Soc. Abs. (206th Natl. Mtg.), MEDI 235 (1993).

T. Graybill, et al., "Preparation and Evaluation of Peptidic Aspartyl Hemiacetals as Reversible Inhibitors of Interleukin-1β Converting Enzyme (ICE)", Int. J. Peptide Protein Res., 44, pp. 173-182 (1994).

Grenier et al., "Functional screening of five PYPAF family members identifies PYPAF5 as a novel regulator of NF-kB and caspase-1," FEBS Letters, 530:73-78 (2002).

S. Hanessian et al., "Design and Synthesis of a Prototype Model Antagonist of Tachykinin NK-2 Receptor", Bioorg. Med. Chem. Lett., 11, 1397-1400 (1994).

Hawkins et al., "Spectrum of clinical features in muckle-wells syndrome and response to Anakinra," Arthritis and Rheumatism, 50(2):607-612 (2004).

Hawkins et al., "Interleukin-1-receptor antagonist in the muckle-wells syndrome," New England Journal of Medicine, 348(25):2584 (2003).

Karanewsky, et al., "Conformationally Constrained Inhibitors of Caspase-1 (Interleukin -1β Converting Enzyme) And of the Human CED-3 Homologue Caspase - 3 (CPP32, Apopain)" Bioorganic & Medicinal Chemistry Letters 8 (1998) 2757-2762.

Layzer, Degenerative Diseases of the Nervous System, Cecil Textbook of Medicine, 20th Edition, vol. 2, pp. 2050-2057, 1996.

MacKenzie, et al., "An inhibitor of the Interleukin Processing Enzyme Blocks IL-1 Release and Reduces Pyrexia and Acute Inflammation" Inflammation Research Associate 7th Internat. Conf. W42 (1994).

B. Miller et al., "Inhibition of Mature IL-1β Production in Murine Macrophages and a Murine Model of Inflammation by WIN 67694, an Inhibitor if IL-1β Converting Enzyme", J. Immunol., 154, pp. 1331-1338 (1995).

A.M.M. Mjalli et al., "Activated Ketones as Potent Reversible Inhibitors of Interleukin-1β Converting Enzyme", Bioorg. Med. Chem. Lett., 4, pp. 1965-1968 (1994).

A.M.M. Mjalli et al., "Phenylalkyl Ketones as Potent Reversible Inhibitors if Interleukin-1β Converting Enzyme", Bioorg. Med. Chem. Lett., 3, pp. 2689-2692 (1993).

M.D. Mullican et al., "The Synthesis and Evaluation of Peptidyl Aspartyl Aldehydes as Inhibitors of ICE", Bioorg. Med. Chem. Lett., 4, pp. 2359-2364 (1994).

R. Nagaraj et al., "Racemization At Proline Residues During Peptide Bond Formation: A Study of Diastereomeric Mixtures of Synthetic Alamethicin Fragments by 270 MHz 1H NMR." Tetrahedron vol. 37, pp. 2001-2005, (1981).

R. Nagaraj et al., "Solution Phase Synthesis of Alamethicin I." Tetrahedron vol. 37, pp. 1263-1270, (1981).

Okamoto et al., Peptide Based ICE Inhibitors: Synthesis, Structure Activity Relationships and Crystallographic Study of the ICE-inhibitor Complex, Chem. Pharm. Bull., 47(1), pp. 11-21, Jan. 1999.

M. Pennington & N. Thornberry, "Synthesis of a Fluorogenic Interleukin-1β Converting Enzyme Substrate Based on Resonance Energy Transfer", Pept. Res., 7, pp. 72-76 (1994).

Prasad et al., "P1 Aspartate-Based Peptide Alpha-Arylacyloxy- and alpha-aryloxymethyl ketones as potent time-dependent inhibitors of Interleukin-1beta converting enzyme" Am. Chem. Soc. Abs. 24th Med. Chem. Symp. 66 (1994).

Ravizza T, Lucas SM, Balosso S, Bernardino L, Ku G, Noe F, Malva J, Randle JC, Allan S, Vezzani A. Abstract Inactivation of caspase-1 in rodent brain: a novel anticonvulsive strategy. Epilepsia. Jul. 2006;47(7):1160-8.

C. Ray et al., "Viral Inhibition of Inflammation: Cowpox Virus Encodes an Inhibitor of the Interleukin-1β Converting Enzyme", Cell, 69, pp. 597-604 (1992).

L. Reiter, "Peptidic p-Nitroanilide Substrates of Interleukin-1β-Converting Enzyme", Int. J. Pept. Protein Res., 43, pp. 87-96 (1994).

L. Revesz et al., "Synthesis of P1 Aspartate-Based Peptide Acyloxymethyl and Fluoromethyl ketones as Inhibitors of Interleukin-1β-Converting Enzyme", Tetrahedron Lett., 35, pp. 9693-9696 (1994).

R.P. Robinson and K.M. Donahue, "Synthesis of a Peptidyl Difluoro Ketone Bearing the Aspartic Acid Side Chain: An Inhibitor of Interleukin-1β Converting Enzyme", J. Org. Chem., 57, 7309-7314 (1992).

S. Schmidt et al., "Synthesis and Evaluation of Aspartyl alpha-Chloro-, alpha-Aryloxy-, and alpha-Arylacyloxymethyl Ketones as Inhibitors of Interleukin-1beta Converting Enzyme," Am. Chem. Soc. Abs. (208th Natl. Mtg.), MEDI 4 (1994).

Simone, Oncology: Introduction, Cecil Textbook of Medicine, 20th Edition, vol. 1, pp. 1004-1010, 1996.

P. Sleath et al., "Substrate Specificity of the Protease that Processes Human Interleukin-1β", J. Biol. Chem., 265, pp. 14526-14528 (1990).

AF Spatola, "Chemistry and Biochemistry of Amino Acids Peptides, and Proteins", 7, ch. 5, pp. 267-281, Weinstein, B., ed., Marcel Dekker, Inc., New York, (1983).

Stack JH, Beaumont K, Larsen PD, Straley KS, Henkel GW, Randle JC, Hoffman HM. Free Full Text IL-converting enzyme/caspase-1 inhibitor VX-765 blocks the hypersensitive response to an inflammatory stimulus in monocytes from familial cold autoinflammatory syndrome patients. J Immunol. Aug. 15, 2005; 175(4):2630-4.

Thakur, et al., "Caspase-1 Inhibitor Reduces Severity of Pseudomonas aeruginosa Keratitis in Mice," Invest Ophthalmol Vis Sci., 2004; 45:3177-3184.

N. Thornberry et al., "Inactivation of Interleukin-1β Converting Enzyme by Peptide (Acyloxy)methyl Ketones", Biochemistry, 33, pp. 3934-3940 (1994).

Tocci, PubMed Abstract (Vitam. Horm. 53:27-63, 1997.

J. Uhl et al., "Secretion of Human Monocyte Mature IL-1β: Optimization of Culture Conditions and Inhibition by ICE Inhibitors", Inflammation Res., 44, pp. S211-S212 (1995).

C.A. Veale et al., "Orally Active Trifluoromethyl Ketone Inhibitors of Human Leukocyte Elastase", J. Med. Chem. vol. 40, pp. 3173-3181, (1997).

P. Villa et al., "Caspases and Caspase Inhibitors", Trends in Biochemical Sciences, 22, pp. 388-393 (1997).

Wannamaker, et al.; "(S)-1-((S)-2-[[1-(4-Amino-3-chloro-phenyl)-methanoyl]-amino]-3,3-dimethyl-butanoyl)-pyrrolidine-2-carboxylic acid ((2R, 3S)-2-ethoxy-5-oxo-tetrahydro-furan-3-yl)-amide (VX-765), an Orally Available Selective Interleukin (IL)-Converting Enzyme/Casapase-1 Inhibitor, Exhibits Potent Anti-Inflammatory Activities by Inhibiting the Release of IL-1β and IL-18" JPET; 321:509-516 (2007).

Office Action dated Jun. 26, 2008 in U.S. Appl. No. 10/985,641.

Office Action dated Mar. 26, 2008 in U.S. Appl. No. 10/985,641.

Office Action dated Jul. 26, 2007 in U.S. Appl. No. 10/985,641.

Office Action dated Apr. 1, 2008 in U.S. Appl. No. 11/069,895.

* cited by examiner

TREATMENT OF DISEASES USING ICE INHIBITORS

CROSS-REFERENCE TO RELATED APPLICATION

This application claims benefit under 35 U.S.C. § 119(e) of U.S. provisional patent application No. 60/574,993, filed May 27, 2004, the disclosure of which is herein incorporated by reference.

BACKGROUND OF THE INVENTION

Autoinflammatory diseases are a group of related conditions that include Muckle-Wells Syndrome (MWS), Familial Cold Autoinflamammatory Syndrome (FCAS) (also known as Familial Cold Urticaria or FCU), Familial Mediterranean Fever (FMF), Chronic Infantile Neurological Cutaneous and Articular Syndrome (CINCAS), a.k.a. Neonatal Onset Multisystem Inflammatory Disease (NOMID), TNFR1-Associated Periodic Syndrome (TRAPS), Hyper-IgD periodic fever Syndrome (HIDS), and Blau's syndrome (Gumucio et al., Clin. Exp. Rheumatol. 20: S-45-S-53, 2002).

These conditions have distinct genetic and phenotypic characteristics, but share certain features of their clinical presentation, including fever, urticaria, arthralgia, serositis, systemic amyloidosis as common complication, robust acute phase response and prominent neutrophilia in affected tissues.

These conditions are caused by mutations in the genes encoding various proteins involved in cellular signaling, notably those involved in regulation of activation of the interleukin-1β converting enzyme (ICE, a.k.a. caspase-1). ICE is a protease that converts the inactive precursor, pro-interleukin-1β (pro-IL-1β) to the active cytokine interleukin-1β (IL-1β), as well as pro-IL-18 to mature, active IL-1β. Among these modulatory genes & proteins, for example, is the gene CAIS1, which codes for the protein cryopyrin. Mutations of this gene and alteration of cryopyrin alters ICE activation, the consequent processing of pro-IL-1β to IL-1β and causes MWS and FCAS (Hoffman et al., Nat. Genet. 29: 301-305, 2001).

The critical role of IL-1β in the etiology of MWS (and by inference in FCAS, FMF, CINCAS, NOMID, TRAPS, HIDS and other autoinflammatory diseases and conditions) is illustrated by the demonstration that patients with MWS respond to treatment with recombinant human interleukin-1 receptor antagonist (rhuIL-1Ra, anakinra) with a dramatic, rapid and sustained reduction in clinical inflammatory symptoms, reduction of serum amyloid A (an acute phase inflammatory reactant) and urinary excretion of amyloid. This treatment, although effective, is limited in its use because it requires daily injection of the therapeutic agent.

Profound clinical improvement in response to anakinra may be an indicator that IL-1 is the key inflammatory cytokine underlying disease states, and indeed that such disease states are in fact autoinflammatory syndromes whose underlying genetic basis has yet to be determined. Examples include systemic-onset juvenile idiopathic arthritis (soJIA), also known as Still's disease, and the macrophage activation syndrome. The present invention also encompasses these indications.

The present invention describes the use of inhibitors of ICE/caspase-1, whether selective for ICE/caspase-1, or broadly active on a range of other caspases (2-14). This treatment, by inhibiting ICE and inhibiting IL-1β production will reduce the symptoms and other disease conditions of MWS, FCAS, FMF, CINCAS, NOMID, TRAPS, HIDS and other autoinflammatory diseases, conditions or syndromes.

Although anakinra has been shown to be effective in treating Muckle-Wells syndrome, Familial Cold Autoinflammatory Syndrome, Hyper-IgD syndrome and systemic onset Juvenile idiopathic Arthritis, anakinra is a protein and it therefore does not possess ideal pharmaceutical properties. Therefore, there is a need for small molecule, orally-active ICE inhibitors for treating certain diseases. Such compounds would be extremely useful in treating the aforementioned disease states where ICE plays a role.

SUMMARY OF THE INVENTION

The present invention relates to compounds for treating certain diseases associated with autoinflammatory diseases (sometimes referred to as autoinflammatory fever syndromes), Cryopyrin-associated Periodic Syndromes, and related syndromes such as Muckle-Wells Syndrome (MWS), Familial Cold Autoinflammatory Syndrome (FCAS) (also known as Familial Cold Urticaria or FCU), Familial Mediterranean Fever (FMF), Chronic Infantile Neurological Cutaneous and Articular Syndrome (CINCAS), a.k.a. Neonatal Onset Multisystem Inflammatory Disease (NOMID), TNFR1-Associated Periodic Syndrome (TRAPS), Hyper-IgD periodic fever Syndrome (HIDS), and Blau's syndrome. The invention also relates to compounds for treating certain diseases exhibiting profound clinical improvement in response to anakinra. The invention also relates to methods for treating the above diseases.

The invention also relates to methods for identifying agents useful for treating these diseases.

BRIEF DESCRIPTION OF THE FIGURES

In FIG. 3A, serum interleukin-18 was reduced on average by 55% at day 14. In FIG. 3B, serum acute phase reactant proteins serum amyloid A (SAA) and C-reactive protein (CRP) was reduced on average by 75% and 65%, respectively. In FIG. 3C, self-reported patient total symptoms were reduced on average by 60% during treatment. See Example 21.

DETAILED DESCRIPTION OF THE INVENTION

Figure 1A:
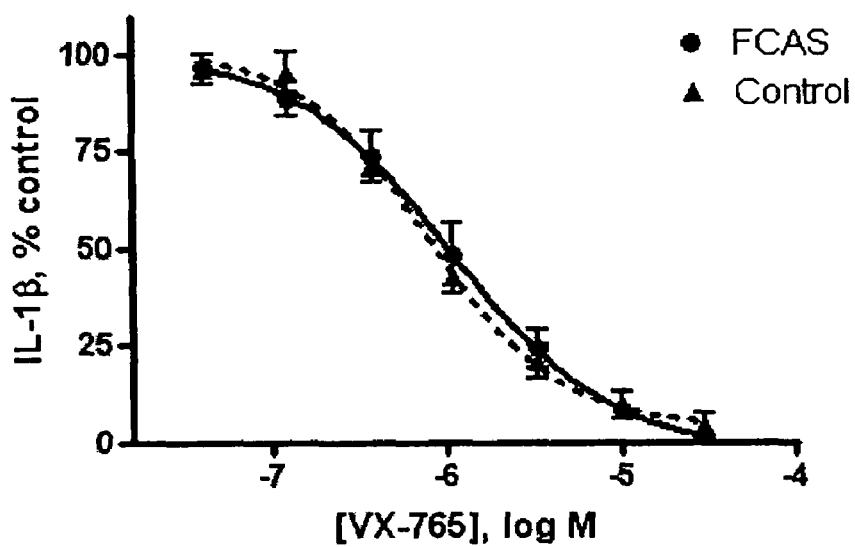
FIGS. 1A-1C depict the in vitro inhibition by compound 7 of IL-1β and IL-18 production by whole blood from patients with FCAS compared with healthy volunteers. See Example 18.

This invention provides compounds disclosed herein and pharmaceutically acceptable derivatives thereof that are particularly effective for ameliorating, treating and/or preventing certain diseases associated with autoinflammatory syndromes and related syndromes, including, but not limited to, Muckle-Wells Syndrome (MWS), Familial Cold Autoinflamammatory Syndrome (FCAS) (also known as Familial Cold Urticaria or FCU), Familial Mediterranean Fever (FMF), Chronic Infantile Neurological Cutaneous and Articular Syndrome (CINCAS), a.k.a. Neonatal Onset Multisystem Inflammatory Disease (NOMID), TNFR1-Associated Periodic Syndrome (TRAPS), Hyper-IgD periodic fever Syndrome (HIDS), and Blau's syndrome, as well as systemic onset juvenile idiopathic arthritis (also known as Still's disease) and macrophage activation syndrome. Symptoms associated with these diseases include, but are not limited to fever, urticaria, arthritis, serositis, systemic amyloidosis, a robust acute phase response, and a prominent neutrophilia in affected tissues.

The compounds according to this invention may be used to treat these disease states in mammals. Any compound that inhibits ICE may be used in the methods and compositions of this invention. Such compounds include those compounds that inhibit ICE selectively and those that inhibit one or more enzyme in the caspase or ICE/CED-3 family.

The compounds of this invention inhibit ICE and/or decrease IL-1, particularly IL-1β and IL-18 levels. These compounds can be assayed, for example, for their ability to inhibit ICE, the production of IL-1β and/or IL-18, the regulation of IL-1 and/or IL-18 levels, and/or affect IL-1β and/or IL-18 activity. Assays for testing each of these activities are known in the art (see Examples herein, WO 95/35308, WO 97/22619, WO 99/47545, or WO 01/90063). Accordingly, these compounds are capable of targeting and inhibiting events in the ICE and/or IL-1 mediated diseases set forth herein.

Compounds that may be used in connection with this invention include, but are not limited to, the compounds of the following documents: WO 04/058718, WO 04/002961, WO 03/088917, WO 03/068242, WO 03/042169, WO 98/16505, WO 93/09135, WO 03/106460, WO 03/103677, WO 03/104231, WO 02/085899, WO 00/55114, WO 00/55127, WO 00/61542, WO 01/05772, WO 01/10383, WO 01/16093, WO 01/42216, WO 01/72707, WO 01/90070, WO 01/94351, WO 02/094263, WO 02/42278, U.S. Pat. No. 6,184,210, U.S. Pat. No. 6,184,244, U.S. Pat. No. 6,187,771, U.S. Pat. No. 6,197,750, U.S. Pat. No. 6,242,422, April 2001 American Chemical Society (ACS) meeting in San Diego, Calif., USA, WO 02/22611, U.S. 2002/0058630, WO 02/12638, WO 95/35308, U.S. Pat. No. 5,716,929, WO 97/22619, U.S. Pat. No. 6,204,261, WO 99/47545, WO 01/90063, U.S. Patent Publication 2004/0014753, U.S. Patent Publication 2004/0009966, U.S. Patent Publication 2003/0236296, U.S. Patent Publication 2003/0096737, U.S. Patent Publication 2003/0092703, U.S. Patent Publication 2002/0169177, U.S. Pat. No. 6,693,096, U.S. Pat. No. 6,610,683, U.S. Pat. No. 6,531,467, U.S. Pat. No. 6,528,506, U.S. Pat. No. 6,200,969, WO 2003/072528, WO 2003/032918, WO 01/00658, WO 98/10778, U.S. Pat. No. 6,716,818, U.S. Pat. No. 6,620,782, U.S. Pat. No. 6,566,338, U.S. Pat. No. 6,495,522, U.S. Pat. Nos. 6,355,618, 6,153,591, WO 2005/003100, WO 2004/002401, WO 00/61542, WO 00/55114, WO 99/47154, U.S. Pat. No. 6,083,981, U.S. Pat. No. 5,932,549, U.S. Pat. No. 5,919,790, U.S. Pat. No. 5,744,451, WO 2002/089749, WO 99/36426, WO 98/16505, WO 98/16504, WO 98/16502, U.S. Pat. No. 6,316,415, U.S. Pat. No. 5,932,549, U.S. Pat. No. 5,919,790, U.S. Pat. No. 5,744,451, EP 1082127, EP 1049703, EP 0932600, EP 0932598, WO 99/56765, WO 93/05071, EP 0600880, and EP 1378573 (which, as set forth herein, are all incorporated by reference herein). In one embodiment, compounds for use in this invention include those of WO 00/55114, WO 00/55127, WO 00/61542, WO 00/61542, WO 01/05772, WO 01/10383, WO 01/16093, WO 01/42216, WO 01/72707, WO 01/90070, WO 01/94351, U.S. Publication 2003/0092703, WO 02/094263, U.S. Publication 2002/0169177, U.S. Pat. No. 6,184,210, U.S. Pat. No. 6,184,244, U.S. Pat. No. 6,187,771, U.S. Pat. No. 6,197,750, U.S. Pat. No. 6,242,422, April 2001 American Chemical Society (ACS) meeting in San Diego, Calif., USA, WO 02/22611, U.S. Publication 2002/0058630, U.S. Publication 2003/0096737, WO 95/35308, WO 97/22619, WO 99/47545, and WO 01/90063. In another embodiment, compounds for use in this invention include those of WO 04/058718, WO 04/002961, WO 95/35308, WO 97/22619, WO 99/47545, and WO 01/90063. Alternately, compounds for use in this invention include those of WO 95/35308, WO 97/22619, WO 99/47545, and WO 01/90063. Preferred compounds are those recited in the claims herein. These compounds may be obtained by methods known to skilled practitioners and the methods disclosed in documents cited herein.

The pharmaceutical compositions and methods of this invention, therefore, will be useful for controlling the levels of IL-1β, IL-18 and other biomarkers and/or activity in vitro or in vivo. The compositions and methods of this invention will thus be useful for controlling the levels of IL-1β, IL-18 and other biomarkers in vivo and for treating or reducing the advancement, severity or effects of certain conditions, including diseases, disorders, or effects as set forth herein.

According to another embodiment, the invention provides a composition comprising a compound of this invention or a pharmaceutically acceptable derivative (e.g., salt) thereof, as described above, and a pharmaceutically acceptable carrier.

According to another embodiment, the compositions of this invention may further comprise another therapeutic agent. Such agents include, but are not limited to, a thrombolytic agent such as tissue plasminogen activator and streptokinase, an anti-inflammatory agent, a matrix metalloprotease inhibitor, a lipoxygenase inhibitor, a cytokine antagonist, (including, but not limited to, an antibody or binding protein against TNF, IL-1, IL-6, IL-12, IL-18 or their receptors), a chemokine antagonist, an immunosuppressant, an anti-cancer agent, an anti-viral agent, a cytokine (including, but not limited to, the interleukin-1 receptor antagonist or anakinra), a growth factor, an immunomodulator (e.g., bropirimine, anti-human alpha interferon antibody, IL-2, GM-CSF, methionine enkephalin, interferon alpha, diethyldithiocarbamate, tumor necrosis factor, naltrexone and rEPO), a prostaglandin, or an anti-vascular hyperproliferation compound.

The term "pharmaceutically acceptable carrier" refers to a non-toxic carrier that may be administered to a patient, together with a compound of this invention, and which does not destroy the pharmacological activity thereof.

Pharmaceutically acceptable carriers that may be used in these compositions include, but are not limited to, ion exchangers, alumina, aluminum stearate, lecithin, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In pharmaceutical compositions comprising only a compound of this invention as the active component, methods for administering these compositions may additionally comprise the step of administering to the subject an additional agent. Such agents include, but are not limited to, a thrombolytic agent such as tissue plasminogen activator and streptokinase, an anti-inflammatory agent, a matrix metalloprotease inhibitor, a lipoxygenase inhibitor, a cytokine antagonist (including, but not limited to, an antibody or binding protein against TNF, IL-1, IL-6, IL-12, IL-18 or their receptors), a chemokine antagonist, an immunosuppressant, an anti-cancer agent, an anti-viral agent, a cytokine (including, but not limited to, the interleukin-1 receptor antagonist or anakinra), a growth factor, an immunomodulator (e.g., bropirimine, anti-human alpha interferon antibody, IL-2, GM-CSF, methionine enkephalin, interferon alpha, diethyldithiocarbamate, tumor necrosis factor, naltrexone and rEPO), a prostaglandin, or an anti-vascular hyperproliferation compound. When a second agent is used, the second agent may be administered either as a separate dosage form or as part of a single dosage form with the compounds or compositions of this invention.

The amount of compound present in the above-described compositions should be sufficient to cause a detectable decrease in the severity of the disease, or in ICE inhibition, the levels of IL-1β, IL-18 or other biomarkers, or the activity of IL-1β, IL-18 or other biomarkers.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups can be quaternized with such agents as lower alkyl halides, such as methyl, ethyl, propyl, and butyl chlorides, bromides and iodides; dialkyl sulfates, such as dimethyl, diethyl, dibutyl and diamyl sulfates; long chain halides such as decyl, lauryl, myristyl and stearyl chlorides, bromides and iodides; aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, or central nervous system), increase oral availability, increase solubility to allow administration by injection, alter metabolism and/or alter rate of excretion.

According to a preferred embodiment, the compositions of this invention are formulated for pharmaceutical administration to a subject or patient, e.g., a mammal, preferably a human being. Such pharmaceutical compositions are used to ameliorate, treat or prevent autoinflammatory diseases in a subject and comprise a compound that inhibits ICE and a phramaceutically acceptable carrier.

Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection and infusion techniques. Preferably, the compositions are administered orally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil and castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

If a solid carrier is used, the preparation can be in tablet form, placed in a hard gelatin capsule in powder or pellet form, or in the form of a troche or lozenge. The amount of solid carrier will vary, e.g., from about 25 to 800 mg, preferably about 25 mg to 400 mg. When a liquid carrier is used, the preparation can be, e.g., in the form of a syrup, emulsion, soft gelatin capsule, sterile injectable liquid such as an ampule or nonaqueous liquid suspension. Where the composition is in the form of a capsule, any routine encapsulation is suitable, for example, using the aforementioned carriers in a hard gelatin capsule shell.

A syrup formulation can consist of a suspension or solution of the compound in a liquid carrier for example, ethanol, glycerin, or water with a flavoring or coloring agent. An aerosol preparation can consist of a solution or suspension of the compound in a liquid carrier such as water, ethanol or glycerin; whereas in a powder dry aerosol, the preparation can include e.g., a wetting agent.

Formulations of the present invention comprise an active ingredient together with one or more acceptable carrier(s) thereof and optionally any other therapeutic ingredient(s). The carrier(s) should be "acceptable" in the sense of being compatible with the other ingredients of the formulation and not deleterious to the recipient thereof.

The pharmaceutical compositions of this invention may be orally administered in any orally acceptable dosage form including, but not limited to, capsules, tablets, and aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents known in the art.

It will be recognized by one of skill in the art that the form and character of the pharmaceutically acceptable carrier or diluent is dictated by the amount of active ingredient with which it is to be combined, the route of administration, and other well-known variables.

The above-described compounds and compositions are also useful in therapeutic applications relating to certain diseases.

Such certain diseases include autoinflammatory syndromes such as cryopyrin-associated Periodic Syndromes, (including Muckle-Wells syndrome, Familial Cold Autoinflammatory Syndrome (FCAS, also known as Familial Cold Urticaria or FCU), chronic infantile neurological cutaneous and articular syndrome (a.k.a. neonatal onset multisystem inflammatory disease)), familial mediterranean fever, TNFR1-Associated Periodic Syndrome (TRAPS), Hyper-IgD periodic fever Syndrome (HIDS), and Blau's syndrome. Other autoinflammatory syndromes whose underlying genetic basis has yet to be determined, may include systemic-onset juvenile idiopathic arthritis (soJIA), also known as Still's disease, and the macrophage activation syndrome.

The compounds of this invention can inhibit the release of IL-1, particularly IL-1β and IL-18, and thus can be useful for inhibiting or blocking several pathophysiological effects of certain diseases as set forth herein.

This invention also relates to a therapeutic method for treating certain diseases, specifically autoinflammatory diseases, by (1) inhibiting IL-1, particularly IL-1β and IL-18 release from cells and/or (2) preventing the untoward, toxic or lethal effects of excessively high tissue levels of IL-1, particularly IL-1β and IL-18 in a mammal, including a human. This method comprises administering to a mammal an effective ICE inhibiting quantity of one or more ICE/CED-3 inhibitors. This method also can be used for the prophylactic treatment or prevention of certain diseases amenable thereto, including Muckle-Wells Syndrome (MWS), Familial autoinflammatory fever syndromes and related syndromes such as Cryopyrin-associated Periodic Syndromes, Cold Autoinflammatory Syndrome (FCAS, also known as Familial Cold Urticaria or FCU), Familial Mediterranean Fever (FMF), Chronic Infantile Neurological Cutaneous and Articular Syndrome (CINCAS), a.k.a. Neonatal Onset Multisystem Inflammatory Disease (NOMID), TNFR1-Associated Periodic Syndrome (TRAPS), Hyper-IgD periodic fever Syndrome (HIDS), Blau's syndrome, systemic onset juvenile idiopathic arthritis, Still's disease and macrophage activation syndrome. The invention provides a method for the treating these disorders by administering to a mammal, including a human, in need thereof an effective amount of such compounds.

The compounds, by inhibiting ICE and blocking the release of IL-1, particularly IL-1β and IL-18 or decreasing IL-1, particularly IL-1β and IL-18 levels and activity, as well as the pathophysiologic actions of excessive levels of IL-1, particularly IL-1β and IL-18 in each of these circumstances, directly facilitate the arrest or resolution of certain diseases, and facilitates the restoration of normal function. Together, these actions relate their novel use in treating certain diseases.

ICE inhibition may be measured by methods known in the art and as described more fully herein.

The phrase "inhibiting the release of IL-1, particularly IL-1β, and IL-18" means:
  a) a decrease of in vivo IL-1β and/or IL-18 levels in a mammal such as a human;
  b) a down regulation of IL-1, particularly IL-1β, and IL-18 levels in vitro or in-vivo; or
  c) a down regulation of IL-1, particularly IL-1β, and IL-18 activity, by direct inhibition of the synthesis of IL-1β and IL-18 or a post-translation event in vivo or in vitro as well as indirect inhibition of IL-1α.

The compounds may be useful in inhibiting the release of IL-1, particularly IL-1β, and IL-18 release by monocytes, macrophages, neuronal cells, endothelial cells, epidermal cells, mesenchymal cells (for example: fibroblasts, skeletal myocytes, smooth muscle myocytes, cardiac myocytes) and many other types of cells.

The term "condition" or "state" refers to any disease, disorder, or effect that produces deleterious biological consequences in a subject.

The level of IL-1, particularly IL-1β, and IL-18 protein in the blood or cell of a patient or a cell culture (i.e., within the cell or the cell culture media) can be determined by for example, assaying for immunospecific binding to IL-1β or IL-18 or to other proteins known to be produced as a result of the presence of active IL-1β and IL-18, including, but not limited to, IL-1α. Such methods are known in the art. For example, immunoassays which can be used include, but are not limited to competitive and non-competitive assay systems, western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays and FACS analysis with labeled antibodies. Such assays well known in the art (see, e.g., Ausubel et al, eds, 1994, Current Protocols in Molecular Biology, Vol. 1, John Wiley & Sons, Inc., New York, which is incorporated by reference herein in its entirety).

Competitive binding assays can also be used to determine the level of IL-1, particularly IL-1β, and IL-18. One example of a competitive binding assay is a radioimmunoassay comprising the incubation of labeled proteins from cells expressing IL-1, particularly IL-1β, and IL-18 (e.g., $^3$H or $^{125}$I) with an IL-1β or IL-18 antibody in the presence of increasing amounts of unlabeled IL-1β or IL-18, and the detection of the IL-1β or IL-18 antibody bound to the labeled IL-1β or IL-18. The affinity of the antibody of interest for a particular antigen and the binding off-rates can be determined from the data by Scatchard plot analysis. Competition with a second antibody can also be determined using radioimmunoassays. In this case, the antigen is incubated with antibody of interest conjugated to a labeled compound (e.g., $^3$H or $^{125}$I) in the presence of increasing amounts of an unlabeled second antibody.

IL-1β or IL-18 levels can also be assayed by activity, for example, IL-1 levels can be assayed by a cell line that is capable of detecting bioactive levels of cytokines like IL-1β or IL-18 or a growth factor. According to one embodiment, the level of bioactive IL-1β in a biological sample is detected by incubating a cell line genetically engineered with isopropyl-β-D-thiogalactopyranoside. The cell line is incubated with the sample to be tested and cell death in the cell line is monitored by determining the intensity of blue color, which is indicative of a bioactive cytokine or growth factor in the sample tested. See also, e.g., Burns (1994) 20(1):40-44 for IL-1 activity assay of serum of patients.

Dosage levels of between about 0.01 and about 100 mg/kg body weight per day, preferably between about 0.5 and about 75 mg/kg body weight per day and most preferably between about 1 and about 50 mg/kg body weight per day of the active ingredient compound are useful in a monotherapy.

In another embodiment, dosage levels of between about 2 and about 200 mg/kg body weight per day, preferably between about 6 and about 100 mg/kg body weight per day and most preferably between about 25 and about 100 mg/kg body weight per day of the active ingredient compound are useful in a monotherapy.

According to one embodiment of this invention, an active ingredient compound of this invention is administered to a subject at a dose of between about 20 mg to about 10,000 mg per administration. In another embodiment, an active ingredient compound of this invention is administered to a subject at a dose of between about 300 mg to about 2,400 mg per administration. In yet another embodiment of this invention, an active ingredient compound of this invention is administered to a subject at a dose of between about 600 mg to about 1,800 mg per administration. In a preferred embodiment, a compound of this invention is administered to a subject at a dose of about 900 mg per administration.

Typically, the pharmaceutical compositions of this invention will be administered from about 1 to 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of a compound of this invention and one or more additional therapeutic agents, both the compound and the additional agent should be present at dosage levels of between about 10% to about 80% of the dosage normally administered in a monotherapy regime.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained. When the symptoms have been alleviated to the desired level, treatment may cease. Patients may, however, require intermittent treatment on a long-term basis upon any recurrence or disease symptoms.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular compound and other therapeutic agent, if present, in the composition.

Accordingly, a method for ameliorating, treating or preventing a disease of this invention in a subject comprises the step of administering to the subject any compound, pharmaceutical composition, or combination described herein.

In a preferred embodiment, the invention provides a method of treating a mammal, having one of the aforementioned diseases, comprising the step of administering to said mammal a pharmaceutically acceptable composition described above. In this embodiment, if the patient is also administered another therapeutic agent, it may be delivered together with the compound of this invention in a single dosage form, or, as a separate dosage form. When administered as a separate dosage form, the other therapeutic agent may be administered prior to, at the same time as, or following administration of a pharmaceutically acceptable composition comprising a compound of this invention.

The methods for identifying a compound or composition for treating a disease according to this invention include methods for screening of a plurality of compounds or compositions for their ability to ameliorate the effects of certain disease(s) and/or improve the condition of a patient having certain disease(s) of this invention. According to one embodiment of this invention, high throughput screening can be achieved by having cells in culture in a plurality of wells in a microtiter plate, adding a different compound or composition to each well and comparing the ICE inhibition and/or IL-1 levels and/or activity in each cell culture to the levels or activity present in a cell culture in a control well. Controls that are useful for the comparison step according to this invention include cells or subjects that have not been treated with a compound or composition and cells or subjects have been treated with a compound or composition that is known to have no effect on ICE inhibition or activity. According to one embodiment of this invention, the high throughput screening is automated so that the steps including the addition of the cells to the plate up to the data collection and analysis after addition of the compound or composition are done by machine. Instruments that are useful in the comparison step of this invention, e.g., instruments that can detect labeled objects (e.g., radiolabelled, fluorescent or colored objects) or objects that are themselves detectable, are commercially available and/or known in the art. Accordingly, compounds and compositions according to this invention that are useful for treating the certain disease disclosed herein can be quickly and efficiently screened.

In another embodiment of this invention, a method for identifying a compound or composition for ameliorating, treating or preventing an autoinflammatory disease in a subject comprises administering to said subject a compound that inhibits ICE or a pharmaceutical composition comprising the compound and comparing the ICE inhibition in the subject before and after treatment with the compound. In an alternate embodiment, this invention provides a method for identifying a compound or composition for ameliorating, treating or preventing an autoinflammatory disease in a subject which comprises administering to said subject a compound that inhibits ICE or a pharmaceutical composition comprising the compound and comparing a biomarker for autoinflammatory diseases in said subject before and after treatment with said compound.

The term "biomarker" is a physical, functional, or biochemical indicator, e.g., the presence of a particular metabolite, of a physiological or disease process. According to this invention, certain biomarkers of inflammation may be used to evaluate the response of patients having autoinflammatory diseases listed herein to compounds that inhibit ICE. These inflammatory biomarkers include, but are not limited to, interleukin-1, interleukin-6 (all autoinflammatory diseases), interleukin-8 (all autoinflammatory diseases), interleukin-18, serum amyloid A, C-reactive protein, erythrocyte sedimentation rate (ESR), haptoglobin, TNFalpha, immunoglobins (particularly IgD), ferritin, leukocyte counts, platelet counts and hemoglobin.

Accordingly, this invention also provides a method for reduction of IL-1β, IL-18 or other biomarker in a subject having an autoinflammatory disease comprising the step of administering to said subject a compound that inhibits ICE or a pharmaceutical composition comprising said compound. In one embodiment, the plasma concentration of the compound or composition in the subject is about equal to or greater than an $IC_{50}$ value taught according to this invention (see, e.g., Examples 18 and 19). In another embodiment, the plasma concentration of the compound or composition in the subject is between about 0.2 μM to about 50 μM, or about 0.8 μM to about 6 μM. In yet another embodiment, the reduction of IL-1β, IL-18 or other biomarker in a subject is measured by comparing (a) IL-1β, IL-18 or other biomarker concentrations in said subject before or after treatment with said compound or composition to (b) IL-1β, IL-18 or other biomarker concentrations in said subject during treatment with said compound or composition. According to this invention, the percent reduction of IL-1β, IL-18 or other biomarker in a subject is selected from the group consisting of (a) at least about 50% to about 100% reduction; (b) at least about 50% to about 90% reduction; and (c) at least about 60% to about 90% reduction.

All applications, patents and references disclosed herein are incorporated by reference. In order that this invention be more fully understood, the following preparative and testing examples are set forth. These examples are for the purpose of illustration only and are not to be construed as limiting the scope of the invention in any way.

EXAMPLES

Example 1

[3S/R, (2S)]-5-Fluoro-4-oxo-3-{[1-(phenothiazine-10-carbonyl)piperidine-2-carbonyl]amino}-pentanoic Acid

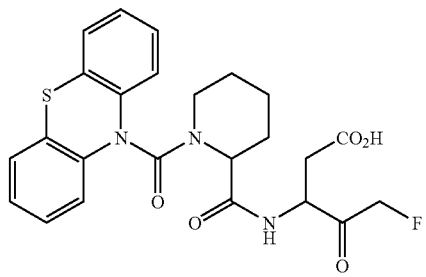

Method A: (S)-(1-Phenothiazine-10-carbonyl)piperidine-2-carboxylic acid methyl ester

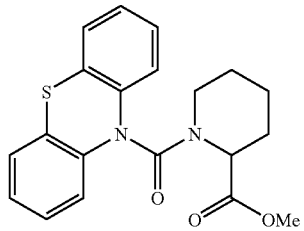

To a stirred solution of methyl pipecolate hydrochloride (1 g, 5.57 mmol) in THF (10 ml) was added phenothiazine carbonyl chloride (1.457 g, 5.57 mmol) followed by diisopropylethylamine (2.02 ml, 11.68 mmol). The resulting solution was stirred for 16 h before being partitioned between ethyl acetate and aq. sat. NH$_4$Cl. The organic layer was washed with brine, dried (MgSO$_4$), filtered and evaporated. The residue was purified by flash chromatography (15% ethyl acetate in hexane) to afford the sub-title compound as a colorless oil which crystallized upon standing (1.823 g, 89%): $^1$H NMR (400 MHz, CDCl$_3$) δ 1.13-1.48 (3H, m), 2.57-2.69 (2H, m), 2.16 (1H, m), 3.00 (1H, m), 3.74 (4H, s+m), 5.00 (1H, m), 7.11 (2H, t), 7.22-7.34 (4H, m), 7.76 (2H, d); $^{13}$C NMR (100 MHz, CDCl$_3$) δ 21.3 (CH$_2$), 24.8 (CH$_2$), 27.3 (CH$_2$), 44.9 (CH$_2$), 52.5 (CH$_3$), 55.9 (CH), 122.8 (CH), 125.5 (CH), 127.8 (CH), 128.0 (CH), 129.2 (C), 141.7 (C), 158.4 (C), 172.2 (C)

Method B: (S)-(1-Phenothiazine-10-carbonyl)piperidine-2-carboxylic Acid

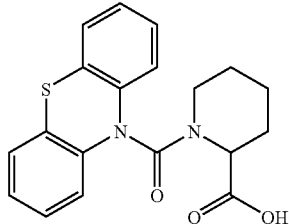

To a stirred solution of (S)-(1-phenothiazine-10-carbonyl)piperidine-2-carboxylic acid methyl ester (0.912 g) in THF (15 ml) and water (8 ml) was added 2M NaOH (3.71 ml) and the reaction mixture was stirred for 16 hours. The reaction mixture was poured into sodium hydrogen carbonate solution (50 ml) and extracted with ethyl acetate (40 ml). Aqueous phase was made acidic and extracted with ethyl acetate (2×75 ml). Organic extracts were combined, dried (MgSO$_4$) and concentrated to give the sub-title compound as a white solid (0.709 g, 81%): $^1$H NMR (400 MHz, CDCl$_3$) δ 0.99-1.72 (5H, m), 2.23 (1H, m), 2.97 (1H, m), 3.58 (1H, m), 4.93 (1H, m), 7.16 (2H, t), 7.28 (2H, t), 7.37 (2H, d), 7.78 (2H, d); $^{13}$C NMR (100 MHz, CDCl$_3$) δ 21.0 (CH$_2$), 24.2 (CH$_2$), 26.7 (CH$_2$), 45.7 (CH$_2$), 56.0 (CH), 123.8 (CH), 126.0 (CH), 127.9 (CH), 128.1 (CH), 130.3 (C), 141.2 (C), 160.1 (C), 175.9 (C).

Method C: [3S/R, 4S/R (2S)]-5-Fluoro-4-hydroxy-3-{[1-(phenothiazine-10-carbonyl)piperidine-2-carbonyl]amino}-pentanoic acid tert-butyl ester

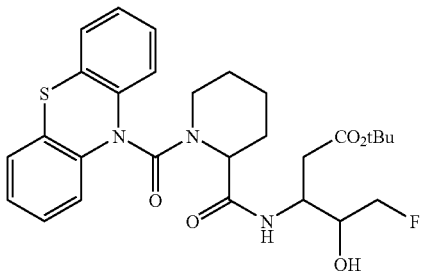

A stirred mixture of (S)-(1-phenothiazine-10-carbonyl)piperidine-2-carboxylic acid (233 mg, 0.658 mmol), 3-amino-5-fluoro-4-hydroxy-pentanoic acid tert-butyl ester (150 mg, 0.724 mmol), HOBt (98 mg, 0.724 mmol), DMAP (88 mg, 0.724 mmol) and anhydrous THF (10 ml) was cooled to 0° C. before EDC (139 mg, 0.724 mmol) was added. The mixture was allowed to warm to room temperature during 16 h then concentrated under reduced pressure. The residue was purified by flash chromatography (50% ethyl acetate in hexane) to afford the sub-title compound as a pale pink foam (294 mg, 82%): $^1$H NMR (400 MHz, CDCl$_3$) δ 1.96 (1H, m), 1.18-1.60 (13H, m), 2.10-2.25 (1H, m), 2.48-2.70 (2H, m), 2.78-2.94 (1H, m), 3.51-4.72 (7H, m), 7.03-7.36 (7H, m), 7.71-7.76 (2H, m); $^{19}$F (376 MHz, CDCl$_3$) δ −228.9 (t), −229.3 (t), −230.1 (t), −230.2 (t).

Method D: [3S/R, (2S)]-5-Fluoro-4-oxo-3-{[1-(phenothiazine-10-carbonyl)piperidine-2-carbonyl]amino}-pentanoic acid tert-butyl ester

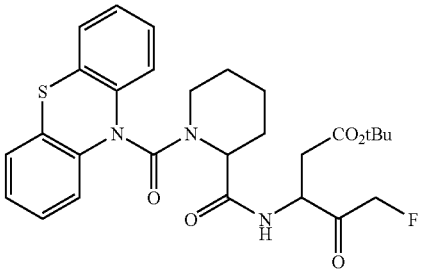

A stirred solution of [3S/R, 4S/R (2S)]-5-Fluoro-4-hydroxy-3-{[1-(phenothiazine-10-carbonyl)piperidine-2-carbonyl]amino}-pentanoic acid tert-butyl ester (294 mg, 0.541 mmol) in anhydrous DCM (10 mL) was treated with 1,1,1-triacetoxy-1,1-dihydro-1,2-benziodoxol-3 (1H)-one (344 mg, 0.812 mmol) at 0° C. The resulting mixture was allowed to warm to room temperature over 2 h, diluted with ethyl acetate, then poured into a 1:1 mixture of saturated aqueous sodium hydrogen carbonate and saturated aqueous sodium thiosulphate. The organic layer was removed and the aqueous layer was re-extracted with ethyl acetate. The combined organic extracts were dried (Na$_2$SO$_4$) and concentrated. The residue was purified by flash chromatography (30% ethyl acetate in hexane) to afford the sub-title compound as a pale pink foam (220 mg, 75%): $^1$H NMR (400 MHz, CDCl$_3$) δ 0.84-0.96 (1H, m), 1.20-1.40 (10H, m+2s), 1.51-1.56 (3H, m), 2.20-2.27 (1H, m), 2.70-2.98 (3H, m), 3.49-3.63 (1H, m), 4.74-5.24 (4H, m), 7.14-7.18 (2H, m), 7.28-7.38 (4H, m), 7.48-7.79 (3H, m); $^{13}$C (100 MHz, CDCl$_3$) δ 20.8/21.0 (CH$_2$), 23.7/23.9 (CH$_2$), 25.8/25.9 (CH$_2$), 28.2/28.3 (CH$_3$), 36.8/36.9 (CH$_2$), 46.0/46.1 (CH$_2$), 52.9 (CH), 56.8 (CH), 82.6 (C), 84.4/84.5 (2d, J 184.0/183.3, CH$_2$F), 123.7/123.8 (CH), 126.1 (CH), 128.0/128.1 (CH), 128.2/128.3 (CH), 130.4/130.5 (C), 141.4 (C), 160.0 (C), 170.0 (C), 171.7 (C), 202.9 (C); $^{19}$F (376 MHz, CDCl$_3$) δ −231.9 (t), −232.2 (t).

Method E: [3S/R, (2S)]-5-Fluoro-4-oxo-3-{[1-(phenothiazine-10-carbonyl)piperidine-2-carbonyl]amino}-pentanoic acid

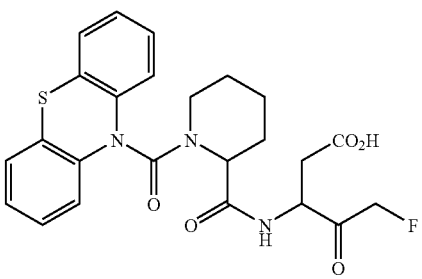

Trifluoroacetic acid (5 mL) was added to a stirred ice cold solution of [3S/R, (2S)]-5-fluoro-4-oxo-3-{[1-(phenothiazine-10-carbonyl)piperidine-2-carbonyl]amino}-pentanoic acid tert-butyl ester (130 mg, 0.24 mmol) in anhydrous DCM (5 mL). The mixture was stirred at 0° C. for 0.5 h then at room temperature for 0.5 h. The mixture was concentrated under reduced pressure and then the residue was dissolved in dry DCM. This process was repeated several times in order to remove excess trifluoroacetic acid. The gum was lyophilized twice from HPLC grade water to afford the title compound as a white powder (77 mg, 66%): IR (solid) 1670, 1716, 1782 cm$^{-1}$; $^1$H NMR (400 MHz, d$_6$-DMSO) δ 0.96-0.99 (1H, m), 1.23-1.26 (2H, m), 1.42-1.44 (1H, m), 1.60 (1H, m), 1.91-1.98 (1H, m), 2.51-2.89 (2H, m), 3.11-3.22 (1H, m), 3.57-3.60 (1H, m), 4.30-4.72 and 5.05-5.29 (4H, 2m), 7.11-7.17 (2H, m), 7.24-7.30 (2H, m), 7.34-7.38 (2H, m), 7.57-7.63 (2H, m), 8.07-8.61 (1H, m); $^{13}$C NMR (100 MHz, DMSO) δ (DMSO+TFA) 18.8/18.9 (CH$_2$), 22.2/22.3 (CH$_2$), 25.8/26.1 (CH$_2$), 31.5/33.2 (CH$_2$), 43.2 (CH$_2$), 50.6/51.1 (CH), 54.4/54.5 (CH), 82.8/82.9 (2d, J 178.6/178.1, CH$_2$F), 119.9/120.0 (CH), 120.4/120.5 (CH), 124.0/124.1 m(CH), 125.9/126.0 (C), 126.4/126.5 (CH), 139.6/139.7 (C), 156.0/156.4 (CO), 170.3 (CO), 170.7/170.8 (CO), 202.2/202.3 (2d, J 14.6/15.1, CO).; $^{19}$F (376 MHz, DMSO) δ chemical shift (multiplicity, relative intensity)-226.7 (t, 3), −226.9 (t, 3), −230.4 (t, 1), −231.2 (t, 1), −232.7 (t, 10), −233.0 (t, 10).

Example 2

[3S/R, (2S)]-3-{[1-(2-Chlorophenothiazine-10-carbonyl)piperidine-2-carbonyl]amino}-4-fluoro-4-oxo-pentanoic Acid

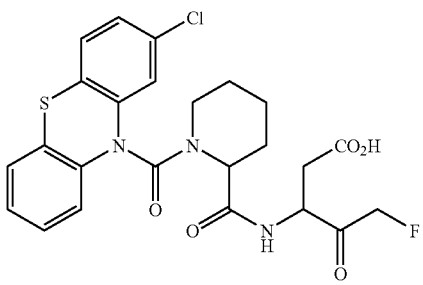

This was prepared from 2-chlorophenothiazine carbonyl chloride using procedures similar to those described above in Methods A-E (73 mg, 69%): IR (solid, cm$^{-1}$) 1738, 1660, 1555, 1363, 1224; $^1$H NMR (400 MHz, d$_6$-DMSO+TFA) δ 0.98-1.61 (4H, m), 1.94-2.03 (1H, m), 2.53-2.89 (2H, m), 3.12-3.24 (1H, m), 3.51-3.61 (1H, m), 4.31-4.73 and 5.10-5.24 (4H, 2m), 7.15-7.49 (6H, m), 7.77-7.81 (1H, m), 8.13-8.64 (1H, m); $^{13}$C NMR (100 MHz, DMSO+TFA) δ 18.7/18.8 (CH$_2$), 22.3/22.6 (CH$_2$), 25.9/26.2 (CH$_2$), 31.5/33.2 (CH$_2$), 43.0/43.2 (CH$_2$), 50.6/51.1 (CH), 54.4/54.5 (CH), 82.8/82.9 (2d, J 178.7/178.3, CH$_2$F), 119.3/119.8 (CH), 120.2/120.3 (CH), 123.6/123.7 (CH), 124.4/124.5 (CH), 124.6/124.8 (C), 126.6 (CH), 126.9 (CH), 127.5 (CH), 131.0 (C), 139.2/139.2 (C), 140.7/140.7 (C), 155.5/155.9 (C), 170.1/170.2 (C), 170.7/170.8 (C), 201.2/201.3 (2d, J 14.3/13.9, CO); $^{19}$F NMR (376 MHz, DMSO+TFA) δ −226.7 (t), −226.9 (t), −230.3 (t), −232.7 (t), −233.0 (t).

Example 3

[3S/R, (2S)]-3-{[1-(3-Chlorophenothiazine-10-carbonyl)piperidine-2-carbonyl]amino}-4-fluoro-4-oxo-pentanoic Acid

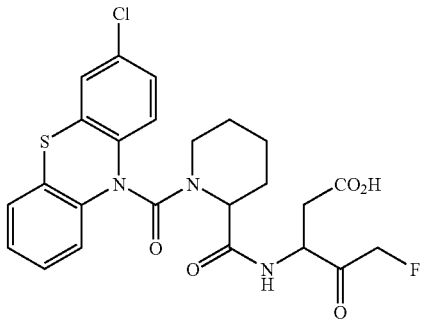

This was prepared from 3-chlorophenothiazine carbonyl chloride using procedures similar to those described above in Methods A-E (108 mg, 65%): IR (solid, cm$^{-1}$) 1737, 1655, 1455, 1373, 1224; $^1$H NMR (400 MHz, d$_6$-DMSO+TFA) δ 0.99-1.61 (5H, m), 1.91-2.04 (1H, m), 2.54-2.90 (2H, m), 3.12-3.24 (1H, m), 3.48-3.60 (1H, m), 4.26-5.28 (4H, m), 7.15-7.68 (7H, m), 8.10-8.62 (1H, m); $^{13}$C NMR (100 MHz, DMSO+TFA) δ 18.8 (CH$_2$), 22.2/22.3 (CH$_2$), 25.8 (CH$_2$), 33.1/33.2 (CH$_2$), 43.2 (CH$_2$), 50.6/51.0 (CH), 54.3/54.4 (CH), 82.7/82.8 (2d, CH$_2$F), 120.2/120.3 (CH), 121.3/121.4 (CH), 124.2/124.3 (CH), 124.8/125.0 (C), 125.7 (CH), 126.3 (CH), 126.6 (CH), 126.8 (CH), 127.7/127.9 (C), 127.9/128.0 (C), 138.5 (C), 139.3 (C), 156.0 (CO), 170.1 (CO), 170.6/170.7 (CO), 201.1/201.2 (2d, CO); $^{19}$F NMR (376 MHz, DMSO+TFA) δ −226.6 (t), −226.9 (t), −232.6 (t), −232.9 (t).

Example 4

[3S/R, (2S)]-3-{[1-(3,4-Dichlorophenothiazine-10-carbonyl)piperidine-2-carbonyl]amino}-4-fluoro-4-oxo-pentanoic Acid

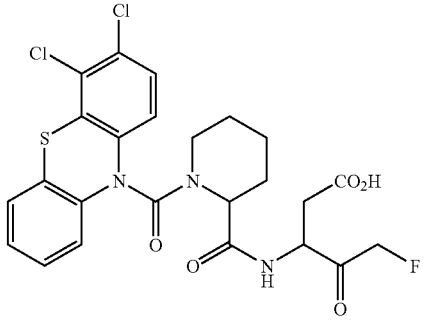

This was prepared from 3,4-dichlorophenothiazine carbonyl chloride using procedures similar to those described above in Methods A-E (91 mg, 66%): IR (solid, cm$^{-1}$) 1737, 1439, 1363, 1219; $^1$H NMR (400 MHz, d$_6$-DMSO+TFA) δ 1.03-1.62 (5H, m), 1.97-2.06 (1H, m), 2.54-2.86 (2H, m), 3.14-3.28 (1H, m), 3.59-3.66 (1H, m), 4.30-5.26 (4H, m), 7.15-7.68 (6H, m), 8.14-8.96 (1H, m); $^{13}$C NMR (100 MHz, DMSO+TFA) δ 20.2 (CH$_2$), 23.8 (CH$_2$), 27.3 (CH$_2$), 34.6/

34.7 (CH$_2$), 44.5 (CH$_2$), 52.1/52.5 (CH), 55.7/55.9 (CH), 84.2/84.3 (2d, CH$_2$F), 120.2/120.3 (CH), 120.8/120.9 (CH), 124.2/124.4 (C), 125.9 (CH), 127.7/127.8 (C), 128.2 (CH), 128.4/128.5 (C), 128.8 (CH), 128.9 (CH), 140.0 (C), 140.1 (C), 140.6 (C), 156.8/156.8 (CO), 171.5 (CO), 172.1/172.1 (CO), 202.6/202.7 (2d, CO); $^{19}$F NMR (376 MHz, DMSO+TFA) δ −226.6 (t), −226.8 (t), −232.6 (t), −232.9 (t).

Example 5

[3S/R, (2S)]-3-{[1-(2,6-Dichlorophenothiazine-10-carbonyl)piperidine-2-carbonyl]amino}-4-fluoro-4-oxo-pentanoic Acid

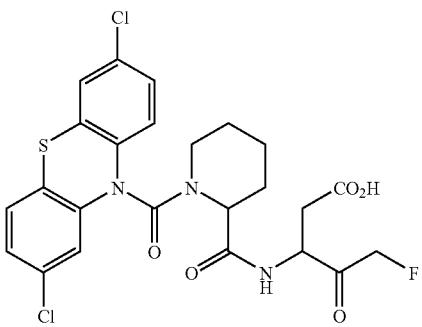

This was prepared from 2.7 g dichlorophenothiazine carbonyl chloride using procedures similar to those described above in Methods A-E (91 mg, 70%): IR (solid, cm$^{-1}$) 1737, 1660, 1555, 1363, 1224; $^1$H NMR (400 MHz, d$_6$-DMSO+TFA) δ 1.02-1.62 (5H, m), 1.91-2.02 (1H, m), 2.53-2.90 (2H, m), 3.13-3.25 (1H, m), 3.51-3.62 (1H, m), 4.31-5.29 (4H, m), 7.22-7.75 (6H, m), 8.18-8.65 (1H, m); $^{13}$C NMR (100 MHz, DMSO+TFA) δ 20.2 (CH$_2$), 23.8 (CH$_2$), 27.3 (CH$_2$), 34.6 (CH$_2$), 44.7 (CH$_2$), 52.5 (CH), 55.8 (CH), 84.3 (d, J 178.2, CH$_2$F), 120.7/121.2 (CH), 122.7/122.8 (CH), 124.7/125.1 (C), 125.3/125.4 (CH), 127.4 (CH), 128.1 (CH), 128.7/128.9 (C), 129.1 (CH), 129.8 (C), 132.7 (C), 139.5/139.6 (C), 141.8/141.9 (C), 157.0 (CO), 171.5 (CO), 172.1 (CO), 202.6 (d, J 14.3, CO); $^{19}$F NMR (376 MHz, DMSO+TFA) δ −226.6 (t), −226.9 (t), −232.6 (t), −232.9 (t).

Example 6

[3S/R, (2S)]-3-{[1-(Carbazole-9-carbonyl)piperidine-2-carbonyl]amino}-4-fluoro-4-oxo-pentanoic Acid

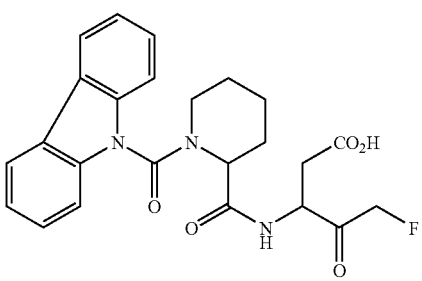

This was prepared from 9-carbazole carbonyl chloride using procedures similar to those described above in Methods A-E (180 mg, 75%): IR (solid, cm$^{-1}$) 1737, 1655, 1419, 1373, 1224; $^1$H NMR (400 MHz, d$_6$-DMSO+TFA) δ 1.36-1.65 (6H, m), 1.94-1.99 (1H, m), 2.12-2.21 (1H, m), 2.59-2.89 (2H, m), 4.32-5.27 (4H, m), 7.30-7.36 (2H, m), 7.48-7.54 (2H, m), 7.63-7.76 (2H, m), 8.17-8.72 (3H, m); $^{13}$C NMR (100 MHz, DMSO+TFA) δ 19.0 (CH$_2$), 23.7/23.8 (CH$_2$), 26.5/26.8 (CH$_2$), 33.3/33.5 (CH$_2$), 44.1 (br, CH$_2$), 50.9/51.4 (CH), 54.5 (br, CH), 82.9/83.1 (2d, J 178.7/178.7, CH$_2$F), 111.0/111.1 (CH), 111.9 (CH), 119.5/119.7 (CH), 120.6/120.7 (CH), 122.5/122.7 (C), 125.8/125.9 (CH), 137.1/137.4 (C), 153.2/153.3 (C), 170.3/170.4 (C), 170.8/170.9 (C), 201.4/201.5 (2d, J 14.6/14.6, CO); $^{19}$F NMR (376 MHz, DMSO+TFA) δ d (J, % I) −226.6 (t, 3), −226.8 (t, 3), −230.0 (t, 1), −232.7 (t, 10), −232.7 (t, 10).

Example 7

[3S/R, (2S)]-5-Fluoro-4-oxo-3-{[1-(6H-phenanthridine-5-carbonyl)-piperidine-2-carbonyl]amino}-pentanoic Acid

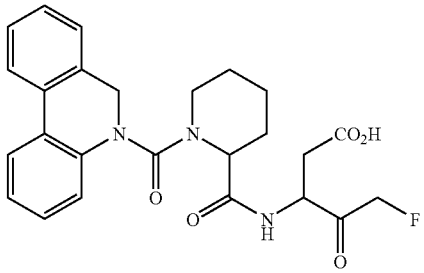

This was prepared from 9,10-dihydrophenanthrinine carbonyl chloride using procedures similar to those described above in Methods A-E (115 mg, 61%): IR (solid, cm$^{-1}$) 1731, 1419, 1363, 1219; $^1$H NMR (400 MHz, d$_6$-DMSO+TFA) δ 1.27-1.69 (5H, m), 1.90-2.06 (1H, m), 2.55-2.87 (2H, m), 3.13-3.21 (2H, m), 4.31-5.26 (6H, m), 7.12-7.48 (6H, m), 7.84-7.86 (2H, m), 8.08-8.58 (1H, m); $^{13}$C NMR (100 MHz, DMSO+TFA) δ 20.5 (CH$_2$), 24.2 (CH$_2$), 27.73 (CH$_2$), 34.6/34.8 (CH$_2$), 44.9 (CH$_2$), 48.5/48.7 (CH), 52.1/52.5 (CH), 55.4/55.7 (CH), 84.2 (d, CH$_2$F), 120.2 (CH), 123.3 (CH), 123.6 (CH), 124.7 (CH), 126.1 (C), 126.3 (CH), 128.0 (CH), 128.3 (CH), 128.7 (CH), 131.6 (C), 134.6 (C), 140.2 (C), 172.1/172.2 (CO), 172.4/172.4 (CO), 203.0 (d, CO); $^{19}$F NMR (376 MHz, DMSO+TFA) δ −226.8 (t), −226.9 (t), −232.7 (t), −232.9 (t).

Example 8

[3S/R,(2S)]-5-Fluoro-3-{2-[(1H-imidazole-2-carbonyl)-amino]-propionylamino}-4-oxo-pentanoic Acid, trifluoroacetate salt (Compound 1)

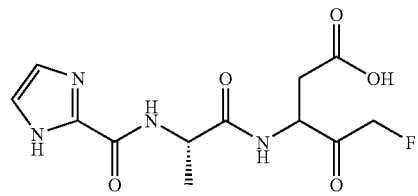

Method A: (2S)-2-[(1H-Imidazole-2-carbonyl)-amino]-propionic Acid Tert-Butyl Ester

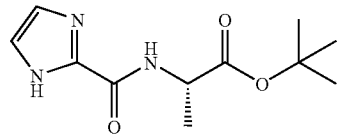

To a solution of 1H-imidazole-2-carboxylic acid (0.179) in N,N-dimethylformamide (DMF) (3 mL) was added alanine tert-butyl ester hydrochloride (0.22 g), diisopropylethyl amine (0.27 mL) and HOBT (0.41 g) before cooling to 0° C. and the reaction mixture was then treated with EDC HCl (0.32 g). The cooling bath was removed and the reaction mixture was stirred at ambient temperature for 18 hrs before being diluted with ethyl acetate and washed with water and brine, dried (MgSO$_4$) and concentrated at reduced pressure. The residue was purified by silica gel chromatography (30% ethyl acetate in hexanes) to afford the sub-title compound as a colourless oil (0.263 g, 73%): $^1$H NMR 400 MHz CDCl$_3$ 1.50 (9H, s), 1.51 (3H, d, J 7.2), 3.70 (1H, m), 7.28 (2H, s), 7.78 (1H, d, J 7.6), 11.49 (1H, br s).

Method B: [3S/R, 4S/R, (2S)]-5-Fluoro-4-hydroxy-3-{2-[(1H-imidazole-2-carbonyl)-amino]-propionylamino}-pentanoic Acid Tert-Butyl Ester

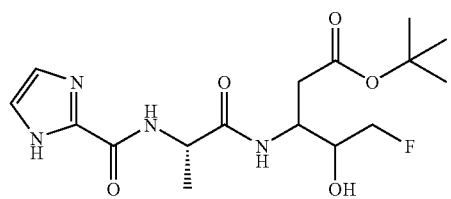

A solution of (2S)-2-[(1H-imidazole-2-carbonyl)-amino]-propionic acid tert-butyl ester (0.257 g) in dichloromethane (2 ml) was cooled to 0° C. before dropwise addition of trifluoroacetic acid and the reaction mixture was warmed to room temperature and stirred for 2 hr before evaporation under reduced pressure. The residue was co-evaporated with dichloromethane (twice) and toluene (twice) to leave the required (2S)-2-[(1H-imidazole-2-carbonyl)-amino]-propionic acid that was used without further purification (0.40 g).

A solution of (2S)-2-[(1H-imidazole-2-carbonyl)-amino]-propionic acid and 3-amino-5-fluoro-4-hydroxy-pentanoic acid tert-butyl ester (0.254 g) in THF (7 mL) was cooled to 0° C. before addition of DMAP (0.151 g), diisopropylethyl amine (0.56 mL), HOBT (0.16 g) and EDC HCl (0.23 g). The reaction mixture was stirred at ambient temperature for 18 hrs before being concentrated at reduced pressure. The residue was purified by silica gel chromatography (5% methanol in dichloromethane) to afford the sub-title compound as a colourless solid (0.386 g, 97%): $^1$H NMR 400 MHz CDCl$_3$/CD$_3$OD 1.40 (12H, m), 3.92 (1H, m), 4.20-4.55 (4H, m), 7.11 (2H, d, J 15); $^{19}$F NMR CDCl$_3$ -229.74 (m), -229.84 (m), -230.54 (m), -230.87 (m).

Method C: [3S/R,(2S)]-5-Fluoro-3-{(2-[(1H-imidazole-2-carbonyl)-amino]-propionylamino}-4-oxo-pentanoic acid tert-butyl Ester

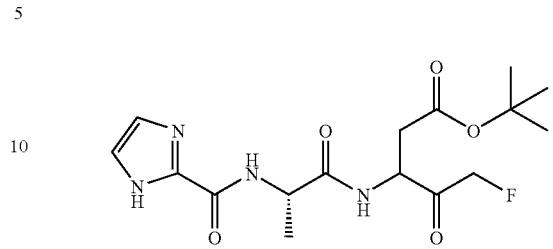

A solution of [3S/R,(2S)]-5-fluoro-4-hydroxy-3-{2-[(1H-imidazole-2-carbonyl)-amino]-propionylamino}-pentanoic acid tert-butyl ester (0.381 g) in dichloromethane was cooled to 0° C. before addition of 1,1,1 triacetoxy-1,1-dihydro-1,2-benziodoxol-3 (1H)-one (0.476 g). The mixture was stirred at room temperature for 2 h before addition of an additional portion of 1,1,1 triacetoxy-1,1-dihydro-1,2-benziodoxol-3 (1H)-one (0.05 g) and reaction mixture was then stirred for 90 min before being concentrated at reduced pressure. The residue was dissolved in ethyl acetate and washed with a 1:1 mixture of aqueous NaHSO$_4$ and aqueous Na$_2$S$_2$O$_3$. The organic layer was collected, dried (MgSO$_4$) and concentrated. The residue was purified by flash chromatography (5% methanol in dichloromethane) to give the sub-title compound as a colourless foam (319 mg, 84%): $^1$H NMR 400 MHz CDCl$_3$ 1.37+1.43 (9H, 2×s), 1.54 (3H, m), 2.85 (1H, m), 3.03 (1H, m), 4.85-5.30 (4H, m), 7.18 (2H, d, J 16), 7.90 (1H, m), 7.98 (1H, m), 11.37+11.45 (1H, 2×s); $^{19}$F NMR 376 MHz CDCl$_3$ -231.85 (t, J 48), -232.12 (t, J 48).

Method D: Compound 1

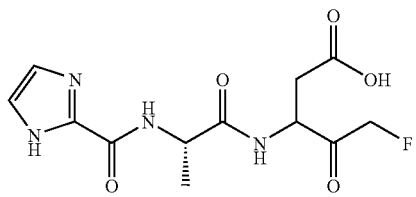

A solution of [3S/R,(2S)]-5-Fluoro-3-{2-[(1H-imidazole-2-carbonyl)-amino]-propionylamino}-4-oxo-pentanoic acid tert-butyl ester (0.31 g) in dichloromethane (2 ml) was cooled to 0° C. before dropwise addition of trifluoroacetic acid and the reaction mixture was warmed to room temperature and stirred for 2 hr before evaporation under reduced pressure. The residue was co-evaporated with dichloromethane (twice) and triturated under ether to give the title compound as a colourless solid (0.35 g): IR 1785.7, 1730.1, 1653.7, 1538.1, 1458.2, 1384.2, 1268.7, 1188.4, 1150.9, 1053.3, 992.13, 931.8, 867.9, 847.0, 768.5 cm$^{-1}$; $^1$H NMR 400 MHz DMSO-d$_6$ 1.37 (3H, d), 2.40-2.85 (2H, m, asp CH$_2$), 4.34-4.75(2.5H, m, 2×CH+0.5CH$_2$F), 5.13-5.41 (1.5H, m, CH$_2$F), 7.50 (2H, s, imidazole CHs), 8.58-8.79 (2H, m, NHs), $^{13}$C NMR 100 MHz DMSO-d$_6$ 18.13, 18.85(ala CH$_3$); 33.13, 34.75(asp CH$_2$), 48.68, 52.41(CHs), 83.46, 85.21(CH$_2$F), 123.67(CH imidazole), 139.57, 158.86, 172.35(m) (C=Os), 202.70(5 peaks ketone); $^{19}$F NMR 376 MHz DMSO-d$_6$ decoupled −75.19 (3F, s, CF₃COOH), −(226.89, 226.96, 230.80, 231.59, 232.95, 233.06 (1F, 6×s, COCH₂F ring opened and ring closed).

Example 9

[3S/R, (2S)]-3-{2-[(1H-Benzoimidazole-2-carbonyl)-amino]-propionylamino}-5-fluoro-4-oxo-pentanoic Acid, trifluoroacetate salt (Compound 2)

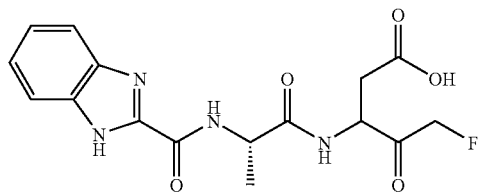

This was prepared from 1H-benzoimidazole-2-carboxylic acid using procedures similar to those described in Methods A-D above (142 mg, 90% for final step): (compound isolated as the TFA salt) off-white solid; IR (solid, cm⁻¹) 3277.9, 1654.6, 1526.6, 1188.6, 1142.5, 1050.4, 927.5, 748.2, 712.4; ¹H NMR (DMSO-d₆) 1.42 (3H, d), 2.51-2.95 (2H, m), 4.21-4.75 (2H, m), 4.76-5.60 (3H, brm), 7.41 (2H, m), 7.65 (2H, m), 8.21-9.05 (2H, m); ¹³C NMR (DMSO-d₆) 18.0, 18.7, 18.8 (Ala CH₃), 37.2, 34.6, 34.7 (Asp CH₂), 47.6, 48.8, 48.85, 49.1 (Asp CH), 52.0, 52.5 (Ala CH), 83.5, 85.2, 85.3, 103.8, 106.0 (CH₂F), 116.6, 123.9 (Aryl CH), 145.3, 145.4, (Aryl C), 158.4, 158.7, 158.8, 172.1, 172.2, 172.4, 172.5, 172.6, 172.7, 173.2 (NC=O), 202.6, 202.7, 202.8, 202.9 (C=O); Found M⁺364.1177. C₁₆H₁₇FN₄O₅ requires M⁺364.1183 (1.8 ppm).

Example 10

[3S/R,(2S)]-5-Fluoro-3-{2-[(1H-imidazole-2-carbonyl)-amino]-butyrylamino}-4-oxo-pentanoic acid, trifluoroacetate salt (Compound 3)

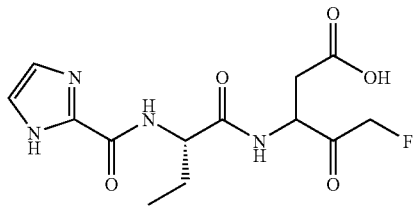

This was prepared from 1H-benzoimidazole-2-carboxylic acid using procedures similar to those described in Methods A-D above (147 mg, 64% for final step): IR(cm⁻¹) 3280.0, 1659.5, 157.9, 1192.5, 1141.6, 784.7, 721.1; ¹H NMR 400 MHz DMSO-d₆ 0.95 (3H, m), 1.78 (2H, m), 2.58-2.98 (2H, m), 4.30-4.78 (2.5H, m), 5.10-5.42 (1.5H, m), 7.41 (2H, s), 8.44+8.75 (2H, 2×m); ¹³C NMR 100 MHz DMSO-d₆ 10.19, 10.29, 15.52 (CH₃), 25.42, 25.49, 26.03, 33.06, 33.13, 34.65, 34.80 (CH₂), 47.45, 47.53, 52.0, 53.96, 54.13 (CH) 65.27 (CH₂), 84.36 (d, J 177, CH₂F), 103.81, 104.00 (C), 123.89 (CH), 139.74 (C=O), 156.90, 158.39, 158.74, 171.51, 171.80, 171.83, 172.02, 173.11 (C=O), 202.51, 202.66, 202.76, 202.90 (CH₂FC=O); ¹⁹F NMR 376 MHz DMSO-d₆ -226.82 (t, J 45), −226.84 (t, J 45), −230.67 (t, J 45), −231.43 (t, J 45), −232.79 (t, J 45), −232.82 (t, J 45).

Example 11

[3S/R,(2S)]-5-Fluoro-3-{2-[(1H-imidazole-2-carbonyl)-amino]-3-methylbutyrylamino}-4-oxo-pentanoic Acid (Compound 4)

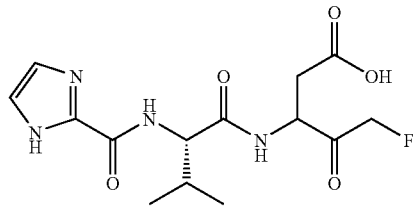

This was prepared from 1H-benzoimidazole-2-carboxylic acid using procedures similar to those described in Methods A-D above (80 g, 85% for final step): white powder, IR (solid, cm⁻¹) 1736, 1649, 1557, 1511, 1455, 1434, 1393; ¹H NMR (DMSO+TFA) 0.92-0.95 (6H, m), 2.06-2.15 (1H, m), 2.56-2.90 (2H, m), 4.33-5.36 (4H, m), 7.79 (2H, s), 8.58-8.90 (2H, m); ¹⁹F NMR (DMSO+TFA) −226.8 (t), −230.6 (t), −231.0 (t), −232.5 (t), −232.6 (t); ¹³C NMR (DMSO+TFA) 18.1/18.4 (CH₃), 19.2/19.3 (CH₃), 34.5/34.8 (CH₂), 51.9/52.2 (CH), 58.5/58.8 (CH), 84.3/84.4 (2d, J 178.7/178.7, CH₂F), 122.0 (CH), 137.5 (C), 153.7 (C), 170.6 (C), 171.9/172.0 (C), 202.5/202.8 (2d, J 14.6/14.6, CO).

Example 12

[3S/R, (2S)]-3-{2-[(1H-Benzoimidazole-2-carbonyl)-amino]-3-methylbutyrylamino}-5-fluoro-4-oxo-pentanoic Acid (Compound 5)

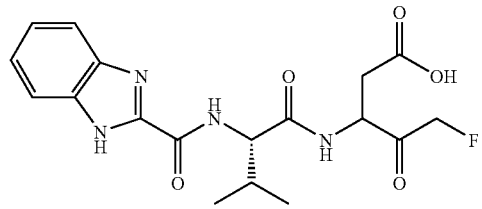

This was prepared from 1H-benzoimidazole-2-carboxylic acid using procedures similar to those described in Methods A-D above (90 mg, 87% for final step): white powder, IR (solid, cm⁻¹) 1737, 1665, 1527, 1373, 1194, 1137; ¹H NMR (DMSO-d₆) 0.90-0.95 (6H, m) 2.15-2.18 (1H, m), 2.59-2.92 (2H, m), 4.33-4.76 and 5.12-5.38 (4H, 2m), 7.31-7.35 (2H, m), 7.66-7.68 (2H, m), 8.36-8.82 (2H, m); ¹⁹F NMR (DMSO+TFA) −226.7 (t), −226.9 (t), −232.4 (t), −232.6 (t); ¹³C NMR (DMSO-d₆) 18.3/18.4/18.5/18.7 (CH₃), 19.4/19.5 (CH₃), 31.0/31.1/31.6 (CH), 34.7/34.8 (CH2), 51.8/52.1 (CH), 57.9/58.3/58.6 (CH), 84.3/84.4 (2d, J 178.7/178.7, CH₂F), 124.0 (CH), 145.2/145.2 (C), 158.4/158.5/158.7/158.8 (C), 170.9/171.1/171.2 (C), 172.0/172.0 (C), 173.1 (C), 173.9 (C), 202.06/202.6 (2d, J 13.8, CO).

Example 13

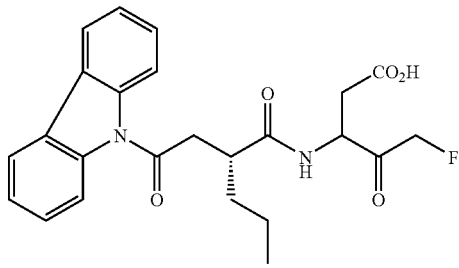

[3S/R(2S)]-3-[2-(Carbazol-9-yl-2-oxo-ethyl)-pentanoylamino]-5-fluoro-4-oxo-pentanoic Acid Method A:
(4S)-Benzyl-3-pentanoyl-oxazolidin-2-one

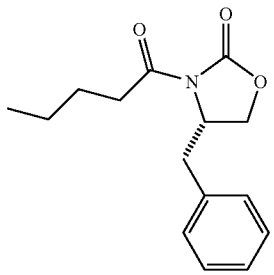

A solution of 4(S)-(−)-benzyl-2-oxazolidinone (10 g, 56.43 mmol) in anhydrous THF (200 ml) at −78° C. was treated with a 2.5M solution of n-butyl lithium in hexanes (23.70 ml, 59.26 mmol) with stirring. The reaction mixture was allowed to stir at −78° C. for 30 min before valeryl chloride (7.57 ml, 62.10 mmol) was added. The reaction mixture was then allowed to warm to ambient temperature over 15 h after which it was diluted with NH$_4$Cl solution, diluted with ethyl acetate and washed with brine. The organic phase was dried (Na$_2$SO$_4$) and concentrated to give a gum. This was purified by flash chromatography (10% EtOAc in 40/60 hexanes) to give the sub-title compound (14.61 g, 99%) as a colourless oil: $^1$H NMR (400 MHz, CDCl$_3$) δ 0.94-1.20 (3H, m), 1.35-1.50 (2H, m), 1.62-1.80 (2H, m), 2.74-2.84 (1H, m), 2.86-3.08 (2H, m), 3.27-3.39 (1H, m), 4.11-4.26 (2H, m), 4.62-4.76 (1H, m), 7.18-7.40 (5H, m).

Method B: [4S(3R)]-3-(4-Benzyl-2-oxo-oxazolidine-3-carbonyl)-hexanoic Acid Tert-Butyl Eester

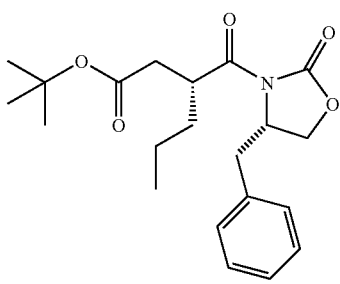

A solution of (4S)-benzyl-3-pentanoyl-oxazolidin-2-one (14.20 g, 54.34 mmol) in THF (100 ml) at −78° C. was treated over 10 min with a 1M solution of sodium bis(trimethylsilyl)amide in THF (59.80 ml, 59.77 mmol) with stirring. The reaction mixture was allowed to stir at −78° C. for 30 min before tert-butyl bromoacetate (10.43 ml, 70.64 mmol) was added. The reaction mixture was then allowed to stir for a further 3.5 h at −78° C. after which it was diluted with NH$_4$Cl solution, diluted with ethyl acetate and washed sequentially with NaHCO$_3$ solution and brine. The organic phase was dried (Na$_2$SO$_4$) and concentrated to give a gum. On standing a white solid was formed and this was recrystallized from 40/60 DCM/hexanes to give the sub-title compound (14.62 g, 72%) as a white solid: $^1$H NMR (400 MHz, CDCl$_3$) δ 0.81-1.20 (3H, m), 1.21-1.76 (13H, m), 2.41-2.55 (1H, m), 2.66-2.92 (2H, m), 3.27-3.40 (1H, m), 4.05-4.26 (2H, m), 4.61-4.72 (1H, m), 7.12-7.40 (5H, m).

Method C: (2R)-2-Propyl-succinic acid 1-benzyl Ester 4-tert-butyl Ester

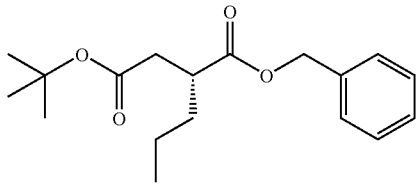

A solution of benzyl alcohol (4.62 ml, 44.64 mmol) in THF (80 ml) at −20° C. was treated with a 2.5M solution of n-butyl lithium in hexanes (13.36 ml, 33.48 mmol) with stirring. The reaction mixture was allowed to warm to −5° C. over 40 min before a solution of [4S(3R)]-3-(4-benzyl-2-oxo-oxazolidine-3-carbonyl)-hexanoic acid tert-butyl ester (8.38 g, 22.32 mmol) in THF (20 ml) was added. The reaction mixture was warmed to ambient temperature over 15 h after which it was diluted with NH$_4$Cl solution and ethyl acetate and washed with brine. The organic phase was dried (Na$_2$SO$_4$) and concentrated to give a gum. This was purified by flash chromatography (11% EtOAc in 40/60 hexanes) to give the sub-title compound (4.56 g, 67%) as a colourless oil: $^1$H NMR (400 MHz, CDCl$_3$) δ 0.83-1.00 (3H, m), 1.21-1.71 (13H, m), 2.34-2.45 (1H, m), 2.75-2.95 (1H, m), 5.09-5.25 (2H, m), 7.30-7.43 (5H, m).

Method D: (2R)-2-Propyl-succinic acid 1-benzyl Ester

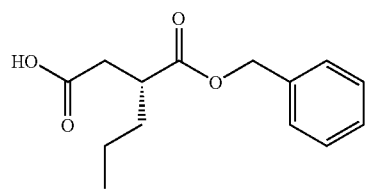

A stirred solution of (2R)-2-propyl-succinic acid 1-benzyl ester 4-tert-butyl ester (4.56 g, 14.88 mmol) in anhydrous DCM (20 ml) at 0° C. was treated with a solution of trifluoroacetic acid (10 ml) in anhydrous DCM (10 ml). The reaction mixture was allowed to warm to ambient temperature over 3 h before being concentrated under reduced pressure. The residue was dissolved in dry DCM, before concentrating again. This process was repeated several times in order to remove excess trifluoroacetic acid to leave the sub-title compound (3.70 g, 99%) as a gum: ¹H NMR (400 MHz, CDCl₃) δ 0.82-0.99 (3H, m), 1.21-1.76 (4H, m), 2.45-2.60 (1H, m), 2.76-3.00 (2H, m), 5.10-5.21 (2H, m), 7.28-7.43 (5H, m), 7.83-8.18 (1H, m).

Method E: (2R)-2-(2-carbazol-9-yl-2-oxo-ethyl)-pentanoic Acid Benzyl Ester

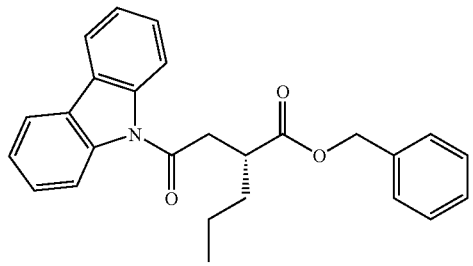

A stirred solution of carbazole (2.49 g, 14.88 mmol) in anhydrous THF (30 ml) at −78° C. was treated with a 1.0M solution of lithium bis(trimethylsilyl)amide in THF (14.88 ml, 14.88 mmol). The reaction mixture was allowed to warm to ambient temperature over 2 h before being re-cooled to −78° C.

A solution of (2R)-2-propyl-succinic acid 1-benzyl ester (3.70 g, 14.78 mmol) in anhydrous DCM (20 ml), stirring at 0° C., was treated with oxalyl chloride (1.43 ml, 16.37 mmol) and DMF (14 drops). The reaction mixture was stirred at 0° C. for 1 h before being concentrated in vacuo. The residue was dissolved in anhydrous THF (10 mL) and added to the lithium anion of carbazole previously prepared at −78° C. The reaction mixture was warmed to ambient temperature over 40 h after which it was diluted with NH₄Cl solution, and ethyl acetate and washed sequentially with 2N HCl, NaHCO₃ solution and brine. The organic phase was dried (Na₂SO₄) and concentrated to give a gum which was purified by flash chromatography (10% EtOAc in 40/60 hexanes) to give the sub-title compound (4.50 g, 76%) as a semi-solid/oil which also contained carbazole: ¹H NMR (400 MHz, CDCl₃) δ 0.82-1.05 (3H, m), 1.11-1.99 (4H, m), 3.18-3.38 (2H, m), 3.56-3.71 (1H, m), 5.10-5.30 (2H, m), 7.11-7.60 (9H, m), 7.92-8.29 (4H, m).

Method F: (2R)-2-(2-carbazol-9-yl-2-oxo-ethyl)-pentanoic acid

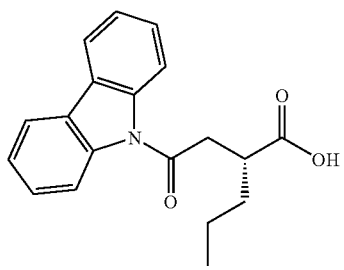

A stirred solution of (2R)-2-(2-carbazol-9-yl-2-oxo-ethyl)-pentanoic acid benzyl ester (4.50 g, 11.26 mmol) in EtOAc (60 ml) was treated with 10% Pd on carbon (~400 mg) and the reaction mixture was then placed under an atmosphere of hydrogen. After 1 h further 10% Pd on carbon (~300 mg) was added and the reaction mixture was placed under hydrogen, with stirring, for a further 3 h after which the reaction mixture was filtered through a celite pad and concentrated to give the sub-title compound (2.94 g, 84%) as a white solid which also contained carbazole: ¹H NMR (400 MHz, CDCl₃) δ 0.92-1.04 (3H, m), 1.32-2.00 (4H, m), 3.19-3.34 (2H, m), 3.58-3.70 (1H, m), 7.30-7.53 (4H, m), 8.00-8.30 (4H, m).

Method G: [3S/R, 4S/R, (2R)]-3-[2-(2-carbazol-9-yl-2-oxo-ethyl)-pentanoylamino]-5-fluoro-4-hydroxy-pentanoic Acid Tert-Butyl Ester

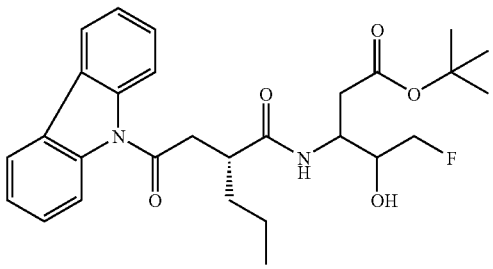

A stirred mixture of (2R)-2-(2-carbazol-9-yl-2-oxo-ethyl)-pentanoic acid (2.94 g, 9.50 mmol), 3-amino-5-fluoro-4-hydroxy-pentanoic acid tert-butyl ester (2.07 g, 9.99 mmol), HOBT (1.41 g, 10.43 mmol), DMAP (1.34 g, 10.97 mmol) and anhydrous THF (40 ml) was cooled to 0° C. before EDC (2.00 g, 10.43 mmol) was added. The mixture was allowed to warm to room temperature during 16 h then concentrated under reduced pressure. The residue purified by flash chromatography (33% EtOAc in 40/60 hexanes) to give the sub-title compound (2.51 g, 53%) as a foam: ¹H NMR (400 MHz, CDCl₃) δ 0.90-1.03 (3H, m), 1.20-1.90 (13H, m), 2.50-3.00 (3H, m), 3.12-3.26 (1H, m), 3.59-3.80 (2H, m), 4.00-4.68 (3H, m), 6.53-6.89 (1H, m), 7.30-7.52 (4H, m), 7.95-8.05 (2H, m), 8.15-8.26 (2H, m); ¹⁹F NMR (376 MHz, CDCl₃) −229.10, −229.34, −230.95, −231.09.

Method H: [3S/R, (2R)]-3-[2-(2-carbazol-9-yl-2-oxo-ethyl)-pentanoylamino]-5-fluoro-4-oxo-pentanoic Acid Tert-Butyl Ester

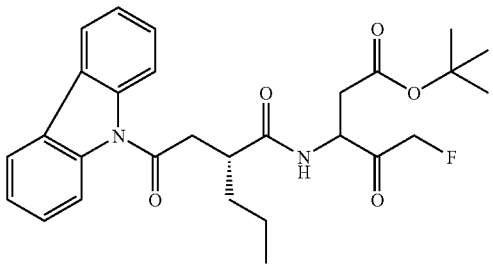

A stirred solution of [3S/R, 4S/R, (2R)]-3-[2-(2-carbazol-9-yl-2-oxo-ethyl)-pentanoylamino]-5-fluoro-4-hydroxy-pentanoic acid tert-butyl ester (2.51 g, 5.03 mmol) in anhydrous DCM (60 ml) was treated with 1,1,1-triacetoxy-1,1- dihydro-1,2-benziodoxol-3 (1H)-one (2.35 g, 5.53 mmol) at 0° C. The resulting mixture was kept at 0° C. for 3 h, diluted with DCM, and then washed sequentially with saturated aqueous sodium thiosulphate, NaHCO₃ solution and brine. The organics were dried (Na₂SO₄) and concentrated. The residue was purified by flash chromatography (25% ethyl acetate in 40/60 hexanes) to afford the sub-title compound as an off white solid (1.437 g, 57%): IR (solid, cm⁻¹) 1722, 1689, 1636, 1531, 1441, 1365, 1279, 1155; ¹H NMR (400 MHz, CDCl₃) δ 0.85-1.50 (3H, m), 1.35-1.54 (11H, m), 1.55-1.69 (1H, m), 1.78-1.95 (1H, m), 2.67-3.28 (4H, m), 3.60-3.79 (1H, m), 4.80-5.59 (3H, m), 6.89-7.04 (1H, m), 7.33-7.54 (4H, m), 7.98-8.04 (2H, m), 8.15-8.28 (2H, m); ¹³C (100 MHz, CDCl₃) δ 14.12, 14.40, 14.47, 14.60, 20.78, 20.84, 21.47, 28.32, 28.42, 28.48, 29.77, 33.63, 34.58, 34.91, 40.05, 43.05, 43.26, 43.29, 52.60, 53.00, 53.64, 66.90, 66.99, 82.62, 82.69, 85.53, 116.88, 116.94, 120.28, 120.31, 124.27, 127.76, 127.86, 128.69, 128.77, 128.99, 138.80, 171.21, 171.29, 172.21, 172.25, 175.53, 176.03, 203.04, 203.20, 203.30, 203.46; ¹⁹F (376 MHz, CDCl₃) δ −232.12, −233.24.

Method I: [3S/R, (2R)]-3-[2-(2-Carbazol-9-yl-2-oxo-ethyl)-pentanoylamino]-5-fluoro-4-oxo-pentanoic Acid

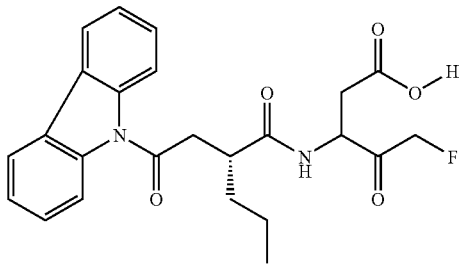

A solution of [3S/R, (2R)]-3-[2-(2-carbazol-9-yl-2-oxo-ethyl)-pentanoylamino]-5-fluoro-4-oxo-pentanoic acid tert-butyl ester (1.43 g, 2.88 mmol) in anhydrous DCM (20 ml) was treated with a solution of TFA (10 ml) in anhydrous DCM (10 ml) with stirring. The mixture was stirred at 0° C. for 2 h then at room temperature for 2 h. The mixture was concentrated under reduced pressure and then the residue was dissolved in dry DCM. This process was repeated several times in order to remove excess trifluoroacetic acid. The off-white solid was recrystallized from Et₂O/40/60 hexanes to give the title compound as a white powder (71 mg): IR (solid, cm⁻¹) 1746, 1689, 1641, 1541, 1436, 1374, 1284, 1207, 1160 cm⁻¹; ¹H NMR (400 MHz, d₆-DMSO) δ 0.80-1.00 (3H, m), 1.20-1.76 (4H, m), 2.30-2.90 (2H, m), 2.95-3.24 (1H, m), 3.26-3.59 (2H, m), 4.24-4.79 (1.5H, m), 5.02-5.43 (1.5H, m), 7.36-7.58 (4H, m), 8.10-8.30 (4H, m), 8.54-8.91 (1H, m); ¹³C NMR (100 MHz, DMSO) δ 14.31, 20.03, 20.13, 21.92, 22.51, 34.36, 34.77, 41.20, 41.62, 44.06, 51.77, 52.84, 83.45, 85.22, 116.70, 120.54, 123.91, 124.01, 127.85, 126.01, 138.20, 172.15, 172.36, 172.96, 173.00, 175.32, 175.48, 202.60, 203.10; ¹⁹F (376 MHz, DMSO) δ −226.68, −226.73, −231.21, −232.95, −233.38, −233.52.

Example 14

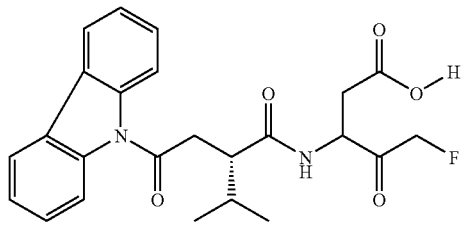

[3S/R(2S)]-3-[2-(2-Carbazol-9-yl-2-oxo-ethyl)-3-methyl-butyrylamino]-5-fluoro-4-oxo-pentanoic Acid This was prepared using procedures similar to those described in Methods A-I. The product was isolated as a white powder (71% for final step): IR (solid, cm⁻¹) 1739, 1682, 1646, 1545, 1447, 1381, 1290, 1209, 1170 cm⁻¹; ¹H NMR (400 MHz, DMSO+TFA) δ 0.79-1.08 (6H, m), 1.89-2.15 (1H, m), 2.31-3.60 (5H, m), 4.21-4.78 (1.25H, m), 4.98-5.45 (1.75H, m), 7.38-7.60 (4H, m), 8.14-8.35 (4H, m), 8.56-8.90 (1H, m); ¹³C NMR (100 MHz, DMSO) δ 20.46, 20.84, 21.04, 21.21, 30.77, 30.85, 33.37, 34.83, 35.24, 38.16, 38.89, 47.67, 48.23, 52.19, 53.43, 83.96, 84.01, 85.72, 85.77, 117.16, 121.02, 124.43, 126.42, 126.52, 128.42, 138.75, 172.64, 172.90, 173.85, 173.90, 174.74, 174.93, 175.16, 202.91, 203.04, 203.51, 203.65; ¹⁹F (376 MHz, DMSO) δ −226.63, −226.68, −231.24, −233.16, −233.38, −233.55.

Biological Methods

Example 15

ICE Inhibition may be measured by methods known in the art.

The effectiveness of ICE inhibitors in the treatment of MWS, FCU, FMF, CINCAS, NOMID, TRAPS, HIDS, systemic onset Juvenile Idiopathic Arthritis, Still's disease and Macrophage Activation Syndrome and other autoinflammatory diseases, conditions or syndromes may be demonstrated by two studies:

Example 16

Blood samples are collected from patients with MWS, FCU, FMF, CINCAS, NOMID, TRAPS, HIDS, systemic onset Juvenile Idiopathic Arthritis, Still's disease and Macrophage Activation Syndrome or other autoinflammatory disease or condition and cultured in vitro as whole blood or processed for the preparation of peripheral blood mononuclear cells (PBMCs). The production of IL-1β is evaluated under normal, unstimulated conditions or in the presence of a stimulus such as lipopolysaccharide, *Staphylococcus aureus*, nigericin or phorbol myristate. ICE inhibitors are added to the cultures at concentrations of 1-100,000 nM to demonstrate their ability to inhibit the production of IL-1p and/or IL-18 by cells from patients with MWS, FCU, FMF, CINCAS, NOMID, TRAPS, HIDS, systemic onset Juvenile Idiopathic Arthritis, Still's disease and Macrophage Activation Syndrome or other autoinflammatory disease, condition or syndrome.

Example 17

Patients with MWS, FCU, FMF, CINCAS, NOMID, TRAPS, HIDS, systemic onset Juvenile Idiopathic Arthritis, Still's disease and Macrophage Activation Syndrome or other autoinflammatory disease or condition are enrolled into a clinical trial to receive treatment with an ICE inhibitor. The drug is administered at a dose of 10-10,000 mg by an appropriate route (oral, intravenous, subcutaneous, etc.) at a dosing frequency of 1-4 times/day or as needed to control the symptoms and other manifestations of the disease, condition or syndrome. Treatment duration may range from periodic use of one or more days to daily use over the life-time of the patient. The efficacy is demonstrated by virtue of their ability to reduce the clinical signs and symptoms, such as fever, urticaria, arthralgia, serositis, systemic amyloidosis, robust acute phase response and prominent neutrophilia in affected tissues.

Example 18

Inhibition by Compound 7 of LPS-Stimulated IL-1β and IL-18 Release from PBMCs of Patients with FCAS Compared with Healthy Controls.

Cryopyrin, the protein encoded by the CAIS1 gene that is mutated in FCAS, modulates ICE/caspase-1 activation and its processing of pro-IL-1β to active IL-1β, as well as pro-IL-18 to active IL-18. It may be expected that the mutated cryopyrin protein would interact differently with ICE/caspase-1 and could alter the ICE/caspase-1 conformation in a way that would alter the interaction of the ICE inhibitor compound with ICE/caspase-1, thus reducing the ability to the compound to inhibit ICE activation and IL-1β and Il-18 processing. Therefore, the experiments of this example were conducted to confirm that compound 7 is able to inhibit ICE in cells of FCAS patients.

FCAS patients from 3 families were studied along with healthy controls. The FCAS patients expressed 3 different CIAS1 gene mutations. Five related patients (mother, two daughters, grand-daughter, and a distant male relative) possessed the common L353P ancestral mutation in cryopyrin that has been described previously (Johnstone R F, Dolen W K, Hoffman H M. A large kindred with familial cold autoinflammatory syndrome. *Ann Allergy Asthma Immunol.* 2003; 90(2): 233-7). The other patients possessed novel mutations that have not been reported. Two patients (mother and daughter) had a T-to-A transition at nucleotide 1976 in the CIAS1 gene, leading to a M659K substitution in cryopyrin. One patient had a G-to-A transition at nucleotide 1573 in the CIAS1 gene, generating a E525K amino acid substitution that has not been reported, as well as the V198M variation described previously in several patients with diverse phenotypes, but also in normal controls. All of the mutations are located in exon 3, which encodes the NBS (NACHT) domain or NBS associated domain, and all are within 3 amino acids of other reported mutations, consistent with studies suggesting mutational hot spots. (Neven B, Callebaut I, Prieur A M, Feldmann J, Bodemer C, Lepore L, Derfalvi B, Benjaponpitak S, Vesely R, Sauvain M J, Oertle S, Allen R, Morgan G, Borkhardt A, Hill C, Gardner-Medwin J. Fischer A, de Saint Basile G. Molecular basis of the spectral expression of CIAS1 mutations associated with phagocytic cell-mediated autoinflammatory disorders CINCA/NOMID, MWS, and FCU. *Blood.* 2004; 103(7): 2809-15).

Whole blood samples were collected from patients with FCAS and from healthy volunteer controls and cultured in vitro. The production of IL-1β was evaluated under normal, unstimulated conditions and in the presence of lipopolysaccharide at a range of concentrations from 10-10,000 ng/mL. Compound 7 was added to the cultures at concentrations of 30-30,000 nM to observe its ability to inhibit the production of IL-1β and IL-18 by cells from patients with FCAS or healthy volunteers. FIG. 1 illustrates the results of these experiments.

More specifically, in FIG. 1A, PBMCs from FCAS patients and normal controls were incubated with 10 ng/ml LPS in the presence of increasing concentrations of compound 7 (0.03-30 μM) for 24 hours. IL-1β in cell culture media was measured by ELISA and the results for each subject were normalized to the level of IL-1β release in the absence of compound 7. Results were reported in mean±SEM, for 3 FCAS patients and 5 control patients. LPS-stimulated IL-1β was inhibited by compound 7 with potency very similar to that of PBMCs from normal subjects ($IC_{50}$ value~1 μM).

Figure 1B:
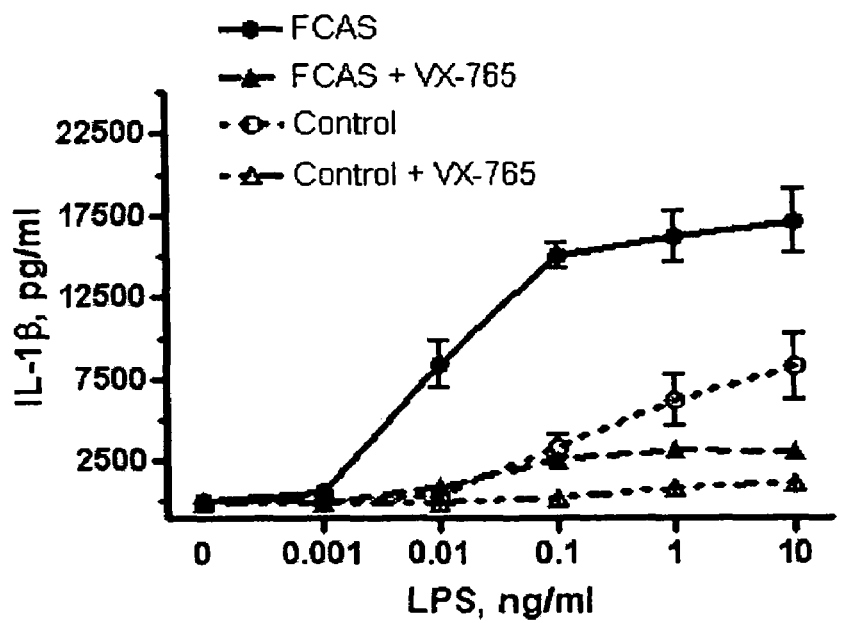

FIG. 1B illustrates the release of IL-1β by PBMCs from FCAS patients or control subjects after exposure to LPS for 24 hours in the absence or presence of 10 μM compound 7. Results were reported in mean±SEM for 7 FCAS patients and 5 control patients. LPS stimulated greater amounts of IL-1β release by PBMCs from FCAS patients than normal subjects and FCAS PBMCs responded to lower concentrations of LPS. Nevertheless, LPS-stimulated IL-1β was inhibited by 10 μM of compound 7 similar to that of PBMCs from normal subjects.

Figure 1C:
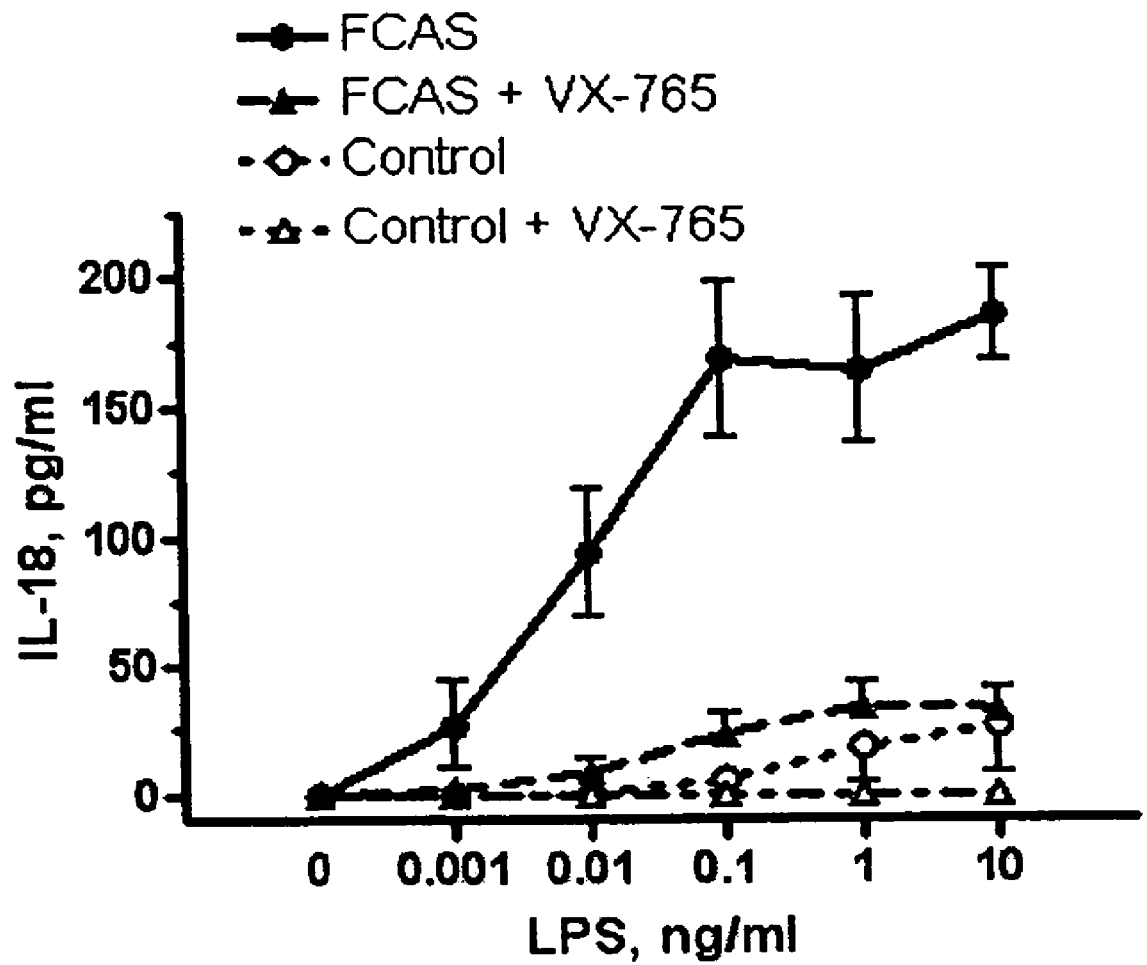

FIG. 1C illustrates the release of IL-18 by PBMCs from FCAS patients or control subjects after 24 hrs exposure to LPS in the absence or presence of 10 μM compound 7. Results were reported in mean±SEM for 3 FCAS patients and 3 control patients. LPS stimulated greater amounts of IL-18 release by PBMCs from FCAS patients than normal subjects and FCAS PBMCs responded to lower concentrations of LPS. Nevertheless, LPS-stimulated IL-18 was inhibited by 10 μM compound 7 to a similar extent as that of PBMCs from normal subjects.

These data demonstrate that FCAS patients exhibited a marked hyper-responsiveness of both IL-1β and IL-18 secretion to LPS stimulation, but no evidence of increased basal secretion of these cytokines, or alterations in basal or stimulated pro-IL-1β levels. Compound 7 blocked IL-1β and IL-18 secretion (FIG. 1) with equal potency in LPS-stimulated cells from FCAS and control subjects. Furthermore, the FCAS patient data presented herein suggests that the mutations of the CAIS1 gene and its encoded cryopyrin protein in FCAS patients do not alter the sensitivity of ICE/caspase-1 to ICE inhibitors like compound 7.

Example 19

Inhibition by Compound 7 of LPS-Stimulated IL-1β Release from PBMCs from 4 MWS Patients Incubated with 10 ng/ml LPS in the Presence of Increasing Concentrations of Compound 7 (0.03-10 μM) for 24 Hour.

As described in Example 18, it may be expected that the mutated cryopyrin protein would interact differently with ICE/caspase-1 and could alter the ICE/caspase-1 conformation in a way that would alter the interaction of the ICE inhibitor compound with ICE/caspase-1, thus reducing the ability to the compound to inhibit ICE activation and IL-1β and Il-18 processing. Therefore, the experiments of this example were conducted to confirm that compound 7 is able to inhibit ICE in cells of MWS patients.

Four MWS patients were studied, three of whom possessed the arginine to tryptophan replacement in position 262 (R262W) and one the threonine to methionine mutation in position 350 (T350M).

Figure 2:
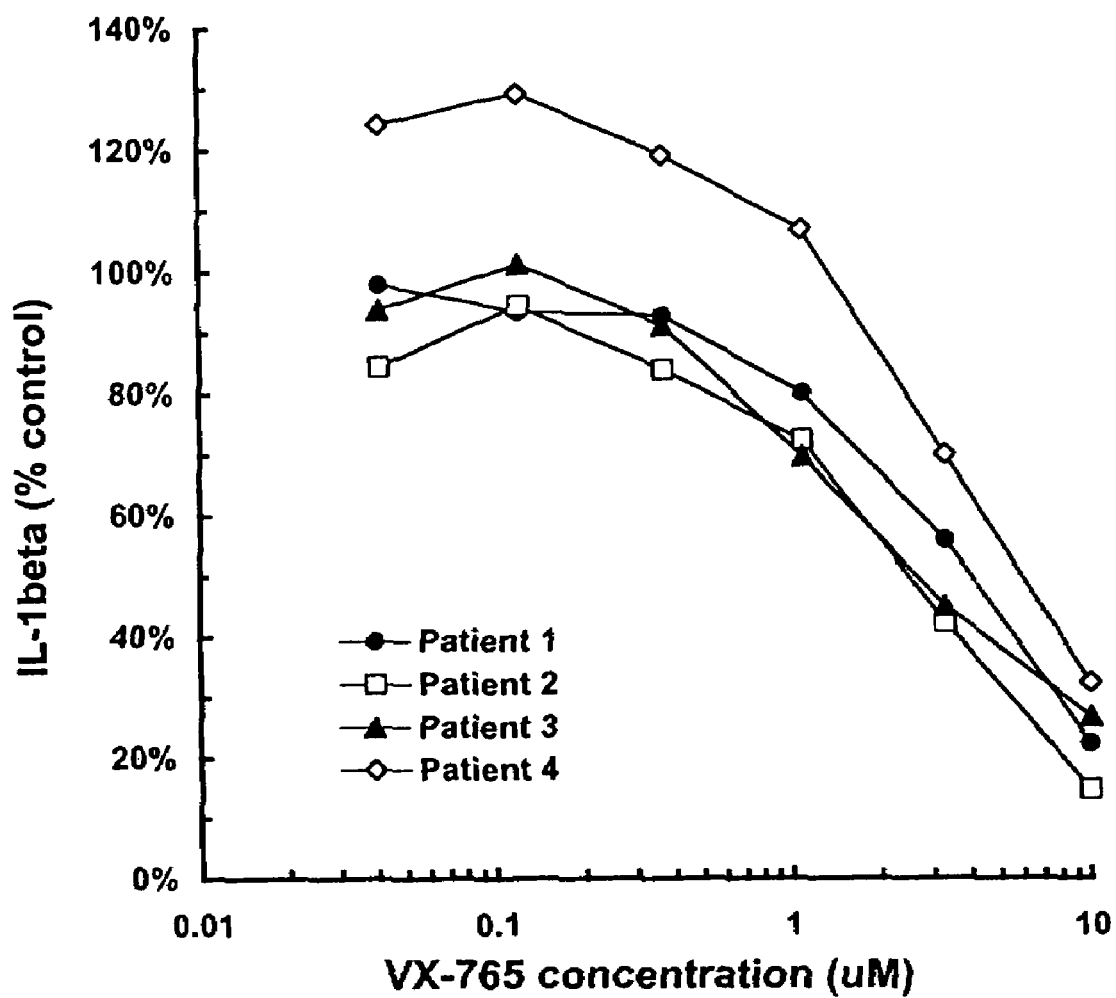
FIG. 2 depicts the in vitro inhibition by compound 7 of IL-1β production by whole blood from patients with MWS. See Example 19.

Whole blood samples were collected from patients with MWS and cultured in vitro. The production of IL-1β was evaluated under normal, unstimulated conditions and in the presence of lipopolysaccharide at a range of concentrations from 10-10,000 ng/mL. Compound 7 was added to the cultures at concentrations of 30-10,000 nM to observe its ability to inhibit the production of IL-1β by cells from patients with MWS or healthy volunteers. FIG. 2 illustrates the results of these experiments.

More specifically, in FIG. 2, IL-1β in cell culture media was measured by ELISA and the results for each subject were normalized to the level of IL-1β release in the absence of compound 7. Results were reported individually for each of the 4 MWS patients. LPS-stimulated IL-1β release by PBMCs from MWS patients was inhibited by compound 7 with potency similar to that of PBMCs from normal subjects (as observed in example 18). This indicates that the cryopyrin mutation in these MWS patients does not alter the ICE/caspase-1 activation in a way that it alters the potency of the interaction of the active metabolite (compound 8) of compound 7 with ICE/caspase-1.

Example 20

Tablet Formation

The composition of compound 7 tablets used in Example 21 below is provided in Table 1. The drug product was formulated to provide 300 mg of compound 7 per tablet.

TABLE 1

Composition of Compound 7 300 mg Tablets

| Component | Quantity (mg/tablet) | Function |
|---|---|---|
| Compound 7 | 300 | Active Ingredient |
| Microcrystalline Cellulose (NF) | 277.50 | Filler |
| Pregelatinized Starch (NF) | 131.25 | Disintegrant |
| Sodium Starch Glycolate (NF) | 15.00 | Disintegrant |
| Colloidal Silicon Dioxide (NF) | 11.25 | Glidant |
| Talc (USP) | 7.50 | Glidant |
| Magnesium Stearate (NF) | 7.50 | Lubricant |
| Total | 750 | |

Example 21

Clinical Response of 4 MWS Patients to 900 mg Compound 7 Administered Orally Three Times Daily for 14 Days.

Four patients with MWS were enrolled into an open-label clinical trial to receive treatment with compound 7. Three of the MWS patients possessed the arginine to tryptophan replacement in position 262 (R262W) and one patient the threonine to methionine mutation in position 350 (T350M).

Compound 7 was administered orally at a dose of 900 mg 3 times daily for 14 days. The anti-inflammatory activity of compound 7 in MWS patients was demonstrated by marked reduction in levels of serum interleukin-18, amyloid A and C-reactive protein during the period of treatment (see FIG. 3). The clinical efficacy of compound 7 was demonstrated by virtue of the reduction in the clinical symptoms reported by the patients, illustrated in FIG. 3 as the sum total of symptoms including rash, fever/chills, arthralgia/myalgia, eye discomfort, fatigue (see FIG. 3). Compound 7 was also well tolerated by the four patients during the 14-day treatment period.

Figure 3A:
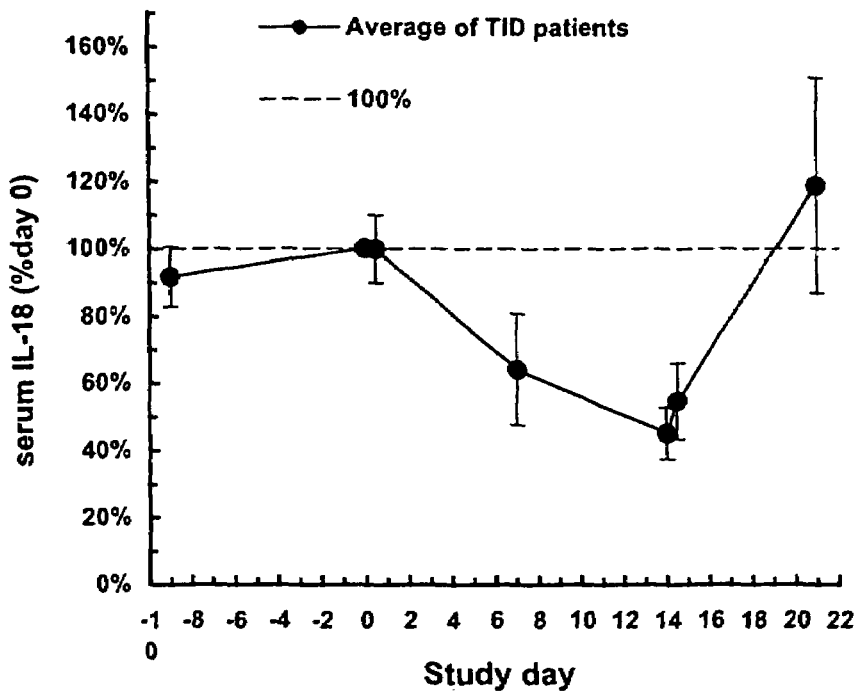
FIGS. 3A-3C depict the clinical response of MWS patients to 14-day treatment with 900 mg compound 7 administered three times daily.

Specifically, in FIG. 3A, serum interleukin-18 (IL-18) was measured before (day −9 and day 0 (first point)), during (day 0 (second point), day 7 and day 14, (first point)) and after (day 14 (second point) and day 21) treatment with compound 7. On average, serum IL-18 levels were reduced by 55% at day 14. Data were reported in mean±SEM from 4 patients. Baseline levels of serum IL-18 were 170-370 pg /mL and were only slightly elevated relative to those typically observed in healthy control subjects.

Figure 3B:
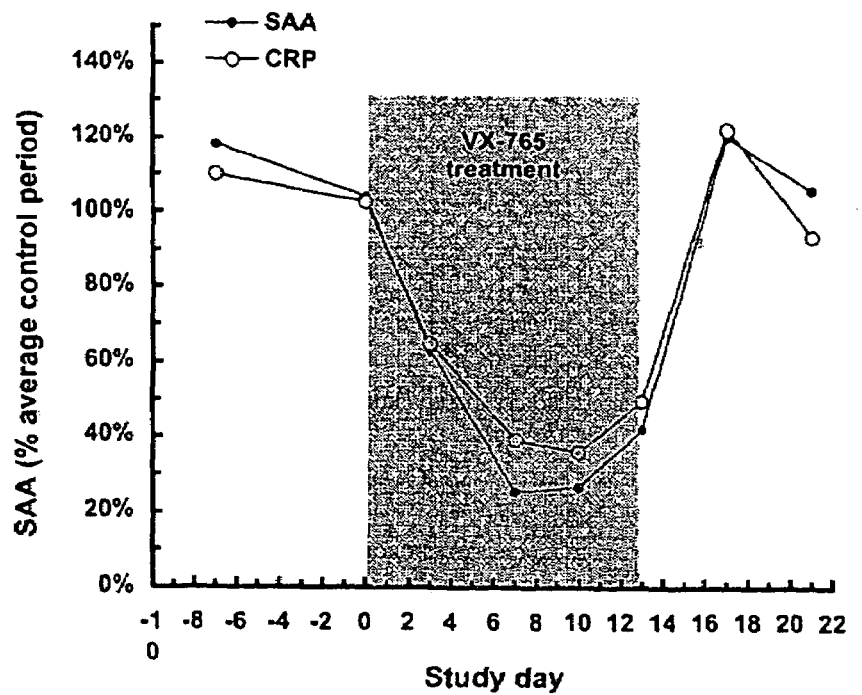

In FIG. 3B, Serum amyloid A (SAA) and C-reactive protein (CRP) were measured before, during and after treatment with compound 7, and the amounts of SAA and CRP were reduced on average by 75% and 65%, respectively. Baseline levels of SAA were 150-650 mg/L and of CRP were 20-90 mg/L, both considerably elevated relative to healthy control subjects.

Figure 3C:
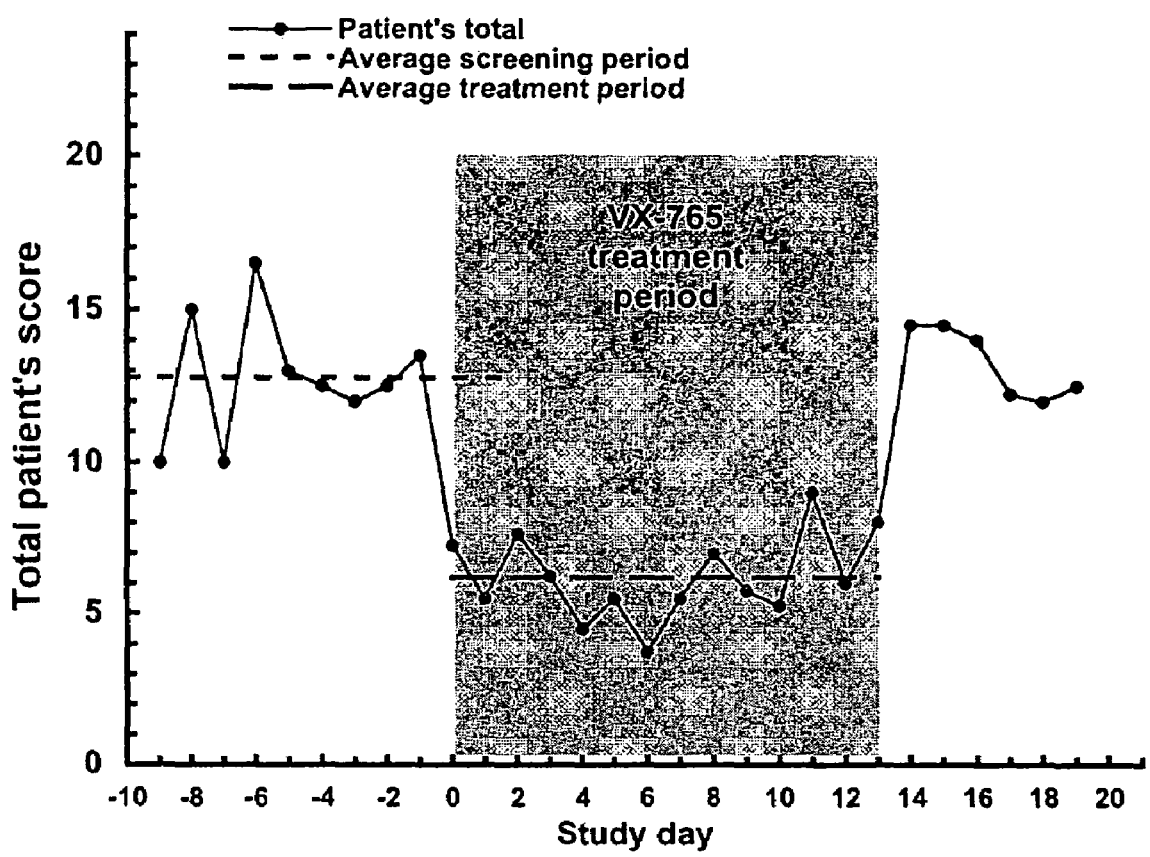

FIG. 3C illustrates that the self-reported patient total symptom scores were reduced on average by 60% during treatment. Individual symptoms (rash, fever/chills, arthralgia/myalgia, eye discomfort, fatigue) were rated daily by patients to be absent (O), minimal (1), mild (2), moderate (3) or severe (4) and the total score was calculated as the sum of individual symptom scores (range 0-20). Patients were experiencing mild-moderate symptoms at the beginning of treatment (scores 10-15), which were reduced to a minimal level (scores about 5) during treatment with compound 7.

Thus, in this example we have demonstrated that an ICE/caspase-1 inhibitor, compound 7, is effective and beneficial in the treatment of an autoinflammatory disease, specifically Muckle-Wells Syndrome, since administration of compound 7 decreases markers of inflammation, including serum interleukin-18, serum amyloid A and serum C-reactive protein and reduces the symptoms of MWS experienced by the patients.

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of example.

What is claimed is:

1. A method for ameliorating or treating Cryopyrin-associated Periodic Syndromes, Muckle-Wells Syndrome, Familial Cold Autoinflammatory Syndrome, Familial Mediterranean Fever, Chronic Infantile Neurological Cutaneous and Articular Syndrome, Neonatal Onset Multisystem Inflammatory Disease, TNFR1-Associated Periodic Syndrome, Hyper-IgD periodic fever Syndrome, Blau's syndrome, systemic onset juvenile idiopathic arthritis, or macrophage activation syndrome in a subject, comprising administering a compound or a pharmaceutical composition comprising said compound to said subject, wherein said compound is

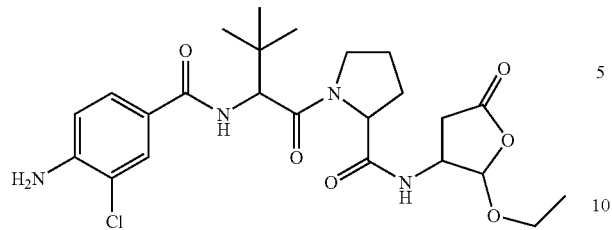

and each stereoisomer
thereof, including:

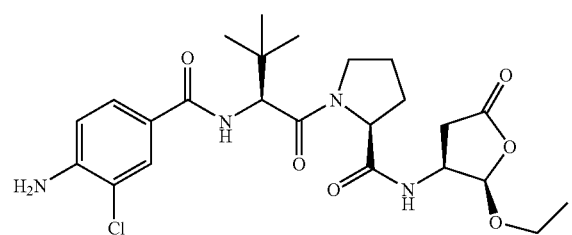

(compound 7)

2. A method for ameliorating or treating Cryopyrin-associated Periodic Syndromes, Muckle-Wells Syndrome, Familial Cold Autoinflammatory Syndrome, Familial Mediterranean Fever, Chronic Infantile Neurological Cutaneous and Articular Syndrome, Neonatal Onset Multisystem Inflammatory Disease, TNFR1-Associated Periodic Syndrome, Hyper-IgD periodic fever Syndrome, Blau's syndrome, systemic onset juvenile idiopathic arthritis, or macrophage activation syndrome in a subject, comprising administering a compound or a pharmaceutical composition comprising said compound to said subject, wherein said compound is:

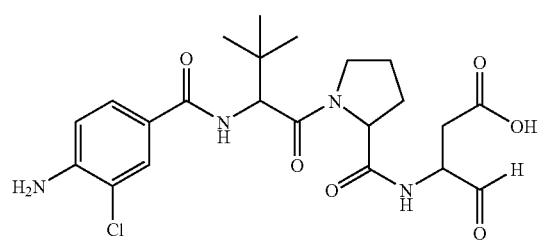

and each stereoisomer thereof, including:

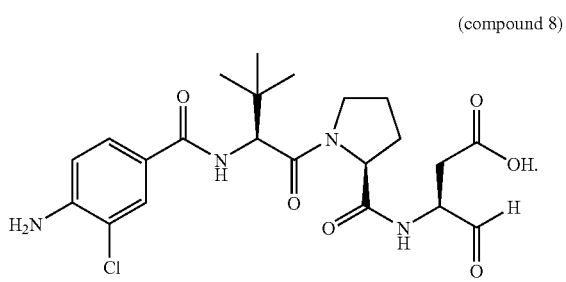

(compound 8)

3. The method according to claim 1 or 2, wherein said compound or said pharmaceutical composition is administered orally, parenterally, by inhalation spray, topically, rectally, nasally, buccally, vaginally or via an implanted reservoir.

4. The method according to claim 1 or 2, wherein said compound or said pharmaceutical composition is used to ameliorate or treat Muckle-Wells Syndrome.

5. The method according to claim 1 or 2, wherein said compound or said pharmaceutical composition is used to ameliorate or treat Familial Cold Autoinflammatory Syndrome.

6. The method according to claim 1 or 2, wherein the compound is administered to the subject at a dose selected from the group consisting of:
   (a) between about 300 mg to about 2,400 mg per administration;
   (b) between about 600 mg to about 1,800 mg per administration; and
   (c) about 900 mg per administration.

7. The method according to claim 1 or 2, wherein the compound is administered to the subject at a dose selected from the group consisting of:
   (a) between about 2 mg per kg body weight to about 200 mg per kg body weight per day;
   (b) between about 6 mg per kg body weight to about 100 mg per kg body weight per day; and
   (c) between about 25 mg per kg body weight to about 75 mg per kg body weight per day.

* * * * *